(12) United States Patent
Brockschmidt, Jr. et al.

(10) Patent No.: US 11,679,169 B2
(45) Date of Patent: Jun. 20, 2023

(54) SYSTEMS AND METHODS FOR PROVIDING POWER TO ULTRAVIOLET LAMPS OF SANITIZING SYSTEMS

(71) Applicant: THE BOEING COMPANY, Chicago, IL (US)

(72) Inventors: Arthur Edward Brockschmidt, Jr., Renton, WA (US); Justin M. Rapozo, Federal Way, WA (US); Erik Jon Haugen, Kent, WA (US)

(73) Assignee: THE BOEING COMPANY, Chicago, IL (US)

( * ) Notice: Subject to any disclaimer, the term of this patent is extended or adjusted under 35 U.S.C. 154(b) by 348 days.

(21) Appl. No.: 17/104,628

(22) Filed: Nov. 25, 2020

(65) Prior Publication Data
US 2021/0386884 A1    Dec. 16, 2021

Related U.S. Application Data

(63) Continuation-in-part of application No. 16/987,514, filed on Aug. 7, 2020.

(60) Provisional application No. 63/037,634, filed on Jun. 11, 2020.

(51) Int. Cl.
*A61L 2/10* (2006.01)
*A61L 2/26* (2006.01)
*H05B 41/38* (2006.01)

(52) U.S. Cl.
CPC .............. *A61L 2/10* (2013.01); *A61L 2/26* (2013.01); *H05B 41/38* (2013.01); *A61L 2202/11* (2013.01); *A61L 2202/16* (2013.01)

(58) Field of Classification Search
CPC .......... A61L 2/10; A61L 2/26; A61L 2202/11; A61L 2202/16; A61L 2202/14; A61L 2202/25; H05B 41/38
See application file for complete search history.

(56) References Cited

U.S. PATENT DOCUMENTS

| | | | |
|---|---|---|---|
| 2004/0061069 A1* | 4/2004 | Schalble | C02F 1/325 250/432 R |
| 2004/0256582 A1 | 12/2004 | Au | |
| 2007/0086912 A1* | 4/2007 | Dowling | C02F 1/325 422/1 |
| 2007/0101867 A1 | 5/2007 | Hunter | |

(Continued)

FOREIGN PATENT DOCUMENTS

| | | |
|---|---|---|
| CA | 2267812 | 1/2000 |
| WO | WO 2016/044759 | 3/2016 |
| WO | WO 2016/057942 | 4/2016 |

OTHER PUBLICATIONS

Extended European Search Report for EP 21178999.5-1202, dated Oct. 8, 2021.

(Continued)

*Primary Examiner* — Bao Q Truong
(74) *Attorney, Agent, or Firm* — The Small Patent Law Group LLC; Joseph M. Butscher

(57) ABSTRACT

A powering device is configured to provide power to an ultraviolet (UV) lamp of a sanitizing system. The powering device includes a power delivery assembly configured to provide power to the UV lamp, and a power controller coupled to the power delivery assembly. The power controller is configured to control one or more aspects of the power provided from the power delivery assembly to the UV lamp.

20 Claims, 17 Drawing Sheets

(56) References Cited

U.S. PATENT DOCUMENTS

| | | | |
|---|---|---|---|
| 2015/0194646 A1* | 7/2015 | Yoshinari | A45F 3/14 |
| | | | 429/187 |
| 2018/0055960 A1 | 3/2018 | Reiber | |
| 2018/0193502 A1 | 7/2018 | Ufkes | |
| 2019/0255201 A1* | 8/2019 | Rosen | A61L 2/0052 |

OTHER PUBLICATIONS

U.S. Appl. No. 17/016,466, filed Sep. 10, 2020.
U.S. Appl. No. 29/735,235, filed May 19, 2020.
U.S. Appl. No. 17/039,011, filed Sep. 30, 2020.
U.S. Appl. No. 17/026,414, filed Sep. 21, 2020.
U.S. Appl. No. 17/020,942, filed Sep. 15, 2020.
U.S. Appl. No. 16/987,514, filed Aug. 7, 2020.
U.S. Appl. No. 16/987,647, filed Aug. 7, 2020.
U.S. Appl. No. 17/026,417, filed Sep. 21, 2020.
U.S. Appl. No. 17/020,951, filed Sep. 15, 2020.
"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.
Communication pursuant to Article 94(3) EPC for EP 21178616.5-1201, dated Jan. 25, 2023.

* cited by examiner

SYSTEMS AND METHODS FOR PROVIDING POWER TO ULTRAVIOLET LAMPS OF SANITIZING SYSTEMS

RELATED APPLICATIONS

This application is a continuation-in-part of U.S. application Ser. No. 16/987,514, entitled "Systems and Methods for Providing Power to Ultraviolet Lamps of Sanitizing Systems," filed Aug. 7, 2020 which relates to and claims priority benefits from U.S. Provisional Patent Application No. 63/037,634, entitled "Systems and Methods for Providing Power to Ultraviolet Lamps of Sanitizing Systems," filed Jun. 11, 2020, each of which is hereby incorporated by reference in its entirety.

Embodiments of the present disclosure generally relate to sanitizing systems, such as may be used to sanitize structures and areas within vehicles, and more particularly to systems and methods of providing power to ultraviolet lamps of the sanitizing systems.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

In order to sanitize a surface of a structure, a known UV light sterilization method emits a broad spectrum UVC light onto the structure. However, UVC light typically takes a significant amount of time (for example, three minutes) to kill various microbes. Further, various microbes may not be vulnerable to UVC light. That is, such microbes may be able to withstand exposure to UVC light.

Also, certain types of microbes may develop a resistance to UVC light. For example, while UVC light may initially kill certain types of microbes, with continued exposure to UVC light over time, the particular species of microbe may develop a resistance to UVC light and be able to withstand UVC light exposure.

Additionally, direct exposure of certain types of UV light may pose risk to humans. For example, certain known UV systems emit UV light having a wavelength of 254 nm, which may pose a risk to humans. As such, certain known UV light disinfection systems and methods are operated in the absence of individuals. For example, a UV light disinfection system within a lavatory may be operated when no individual is within the lavatory, and deactivated when an individual is present within the lavatory.

Further, known UV light sanitizing systems are typically large, bulky, and often require fixed, stationary infrastructure.

SUMMARY OF THE DISCLOSURE

A need exists for a system and a method for providing power to ultraviolet lamps of portable sanitizing systems.

With those needs in mind, certain embodiments of the present disclosure provide a powering device configured to provide power to an ultraviolet (UV) lamp of a sanitizing system. The powering device includes a power delivery assembly configured to provide power to the UV lamp, and a power controller coupled to the power delivery assembly. The power controller is configured to control one or more aspects of the power provided from the power delivery assembly to the UV lamp.

In at least one embodiment, the powering device further includes one or more potentiometers coupled to the power controller and configured to adjust or otherwise control frequency, pulse width modulation, and current with respect to the power provided to the UV lamp.

In at least one embodiment, the powering device further includes a coupler that connects the power delivery assembly to the UV lamp. The coupler may be (or include) a twisted pair of insulated wires. The coupler may be (or include) a coaxial cable including an insulation layer and a metallic shielding layer that surrounds the insulation layer.

In at least one embodiment, the powering device further includes a transformer disposed between the power delivery assembly and the UV lamp.

In at least one embodiment, the power delivery assembly includes an external power interface, a charger, a battery pack, and at least one capacitor. The charger is configured to receive electric current from the external power interface and supply the electric current to at least one of the battery pack or the at least one capacitor.

In at least one embodiment, the powering device further includes a power boost switch selectively actuatable to command a temporary power increase from the power delivery assembly to the UV lamp.

Certain embodiments of the present disclosure provide a method of providing power to an ultraviolet (UV) lamp of a sanitizing system. The method includes providing, by a power delivery assembly of a powering device, power to the UV lamp; and controlling, from a power controller coupled to the power delivery assembly, one or more aspects of the power provided from the power delivery assembly to the UV lamp.

Certain embodiments of the present disclosure provide a powering device configured to provide power to an ultraviolet (UV) lamp of a sanitizing system, the powering device includes a power delivery assembly, a power controller, one or more potentiometers, a transformer, and a coupler. The power delivery assembly includes a battery pack and at least one capacitor and is configured to provide power to the UV lamp. The power controller is coupled to the power delivery assembly and is configured to control one or more aspects of the power provided from the power delivery assembly to the UV lamp. The one or more potentiometers are coupled to the power controller and are configured to adjust or otherwise control frequency, pulse width modulation, and current with respect to the power provided to the UV lamp. The transformer is disposed between the power delivery assembly and the UV lamp. The at least one capacitor is configured to receive electric current from the battery pack and supply the electric current to the transformer. The coupler connects the transformer to the UV lamp. The coupler includes at least one insulated wire that is surrounded by a metallic shielding layer.

DETAILED DESCRIPTION OF THE DISCLOSURE

Figure 1:
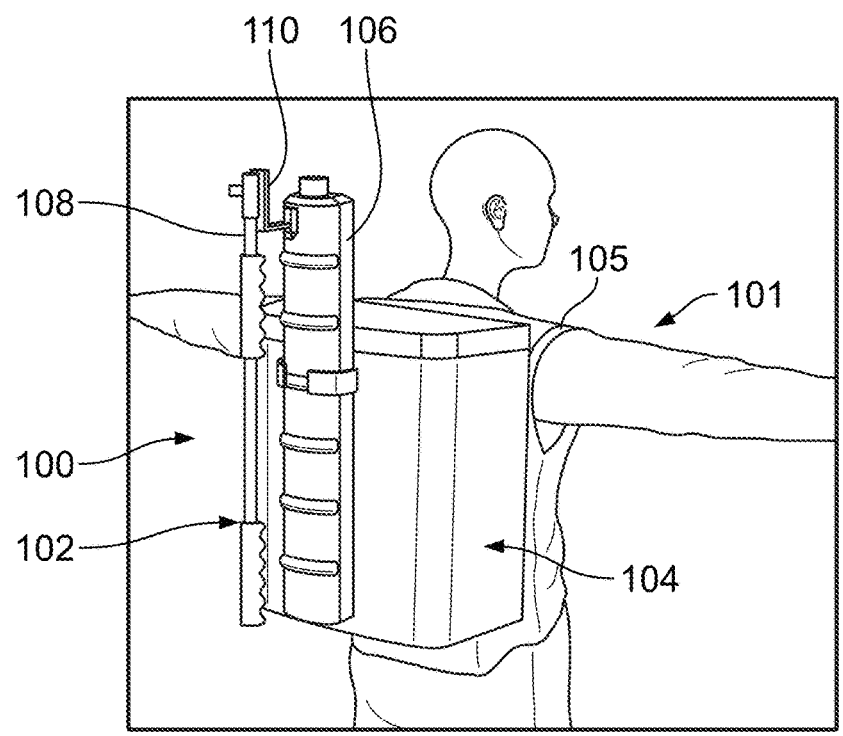
FIG. 1 illustrates a perspective view of a portable sanitizing system worn by an individual, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system and method that includes an ultraviolet (UV) lamp (such as an excimer lamp) that emits UV light in a far UV light spectrum, such as at a wavelength of 222 nm, which neutralizes (such as kills) microbes (for example, viruses and bacteria), while posing no risk to humans. The UV lamp may be used within an internal cabin to decontaminate and kill pathogens. Embodiments of the present disclosure provide safer and more effective sanitation as compared to certain known UV systems. The UV lamp may be used in a portable sanitizing system or a fixed sanitizing system. For example, operating the UV lamp to emit sanitizing UV light having a wavelength of 222 nm may be used with a portable system or a fixed system.

Certain embodiments of the present disclosure provide systems and methods of providing power to UV lamps, such as excimer lamps and metal vapor lamps. In at least one embodiment, the UV lamp is an excimer lamp of a portable sanitizing system.

In at least one embodiment, the systems and methods include a portable powering device that is configured to be used with batteries to provide power to a UV lamp, such as an excimer lamp, that is configured to emit UV light having a wavelength in the far UV wavelength range of the electromagnetic spectrum. For example, the UV lamp is configured to emit UV light having a wavelength between 220 nm and 230 nm, such as 222 nm. In at least one other embodiment, the portable powering device is configured to provide power to a UV lamp, such as a non-excimer metal vapor plasma lamp, that is configured to emit UV light having a wavelength in the UVC wavelength range of the electromagnetic spectrum. For example, the wavelength may be from 230 nm to 280 nm, such as 254 nm.

The portable powering device includes a power source, which may include one or more batteries and/or an external power interface (e.g., electrical plug, connector, adaptor, and/or the like). The portable powering device also includes a power controller that includes one or more potentiometers that are configured to adjust frequency, pulse width modulation, and/or current. The portable powering device also includes one or more switching devices. The one or more switching devices may include an on/off power switch, a power boost switch, and/or an optional UV lamp power switch. An insulated wire of the portable powering device connects to the UV lamp, which may be within a wand assembly.

The portable powering device is configured to provide direct current (DC) voltage to the UV lamp to increase operational efficiency and power output of the UV lamp. The increased efficiency and/or power output can be achieved by the portable powering device varying the frequency and pulse width of the input DC voltage. Adjustments for the system include controlling nominal output power/efficiency, adjusting pulse width frequency and lamp efficiency, and adjusting overcurrent.

In at least one embodiment, the systems and methods are configured to provide power to a UV lamp that requires high voltage. The power controller for the UV lamp is configurable by adjusting one or more potentiometers to provide maximum or otherwise increased UV light output with minimal or reduced amount of power.

FIG. 1 illustrates a perspective view of a portable sanitizing system 100 worn by an individual 101, according to an embodiment of the present disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110.

As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like.

Figure 2:
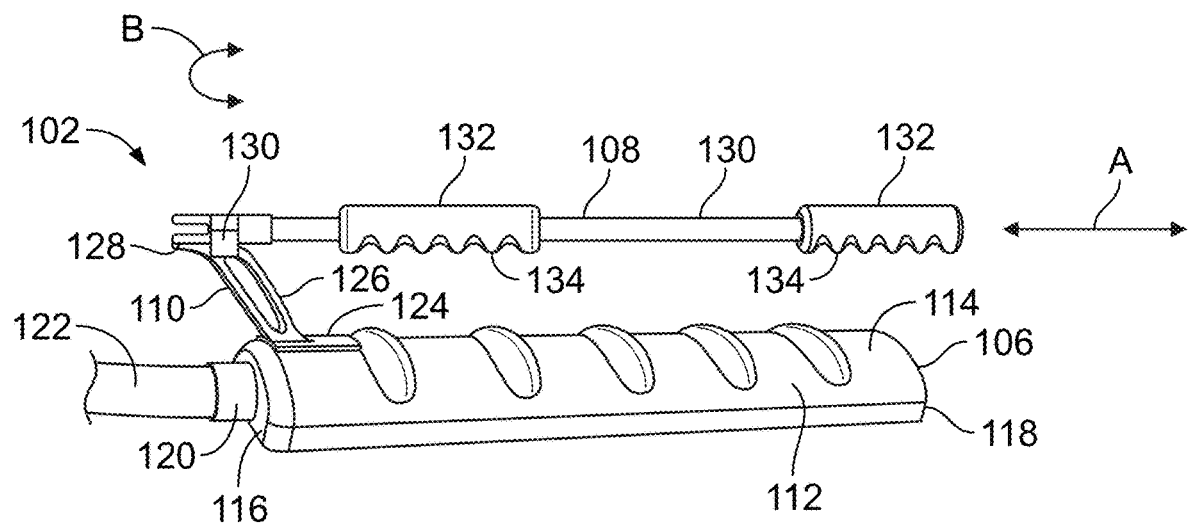
FIG. 2 illustrates a perspective lateral top view of a wand assembly, according to an embodiment of the present disclosure.

FIG. 2 illustrates a perspective lateral top view of the wand assembly 102, according to an embodiment of the present disclosure. The sanitizing head 106 couples to the handle 108 through the coupler 110. The sanitizing head 106 includes a shroud 112 having an outer cover 114 that extends from a proximal end 116 to a distal end 118. As described herein, the shroud 112 contains a UV lamp.

A port 120 extends from the proximal end 116. The port 120 couples to a hose 122, which, in turn, couples to the backpack assembly 104 (shown in FIG. 1). The hose 122 contains electrical cords, cables, wiring, or the like that couples a power source or supply (such as one or more batteries) within the backpack assembly 104 (shown in FIG. 1) to a UV lamp 140 within the shroud 112. Optionally, the electrical cords, cables, wiring, or the like may be outside of the hose 122. The hose 122 also contains an air delivery line, such as an air tube) that fluidly couples an internal chamber of the shroud 112 to an air blower, vacuum generator, air filters, and/or the like within the backpack assembly 104.

The coupler 110 is secured to the outer cover 114 of the shroud 112, such as proximate to the proximal end 116. The coupler 110 may include a securing beam 124 secured to the outer cover 114, such as through one or more fasteners, adhesives, and/or the like. An extension beam 126 outwardly extends from the securing beam 124, thereby spacing the handle 108 from the shroud 112. A bearing assembly 128 extends from the extension beam 126 opposite from the securing beam 124. The bearing assembly 128 includes one or more bearings, tracks, and/or the like, which allow the handle 108 to linearly translate relative to the coupler 110 in the directions of arrows A, and/or pivot about a pivot axle in the directions of arc B. Optionally, the securing beam 124 may include a bearing assembly that allows the sanitizing head 106 to translate in the directions of arrows A, and/or rotate (for example, swivel) in the directions of arc B in addition to, or in place of, the handle 108 being coupled to the bearing assembly 128 (for example, the handle 108 may be fixed to the coupler 110).

In at least one embodiment, the handle 108 includes a rod, pole, beam, or the like 130, which may be longer than the shroud 112. Optionally, the rod 130 may be shorter than the shroud 112. One or more grips 132 are secured to the rod 130. The grips 132 are configured to be grasped and held by an individual. The grips 132 may include ergonomic tactile features 134.

Optionally, the wand assembly 102 may be sized and shaped differently than shown. For example, in at least one embodiment, the handle 108 may be fixed in relation to the shroud 112. Further, the handle 108 may or may not be configured to move relative to itself and/or the shroud 112. For example, the handle 108 and the shroud 112 may be integrally molded and formed as a single unit.

In at least one embodiment, the wand assembly 102 is not coupled to a backpack assembly. For example, the wand assembly 102 is a standalone unit having a power source, such as one or more batteries. As another example, the wand assembly 102 is coupled to a case assembly.

Figure 3:
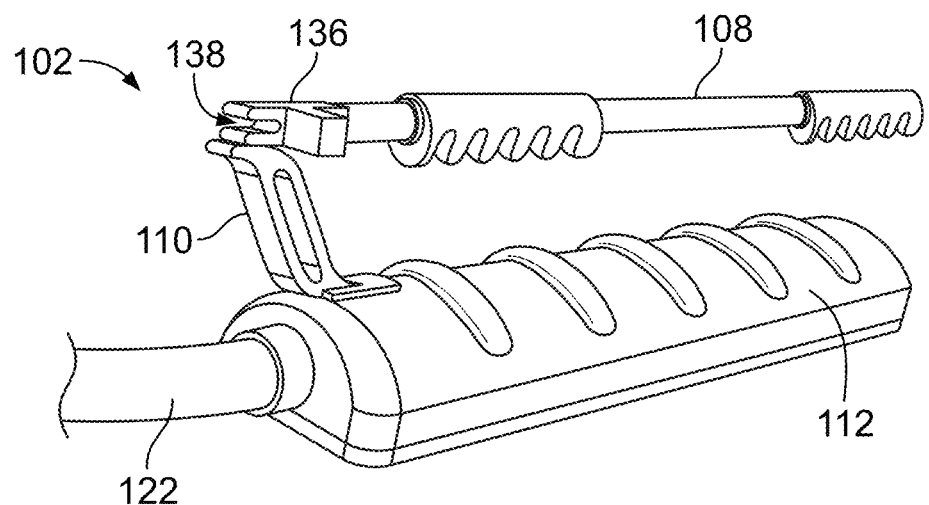
FIG. 3 illustrates a perspective rear view of the wand assembly of FIG. 2.
Figure 4:
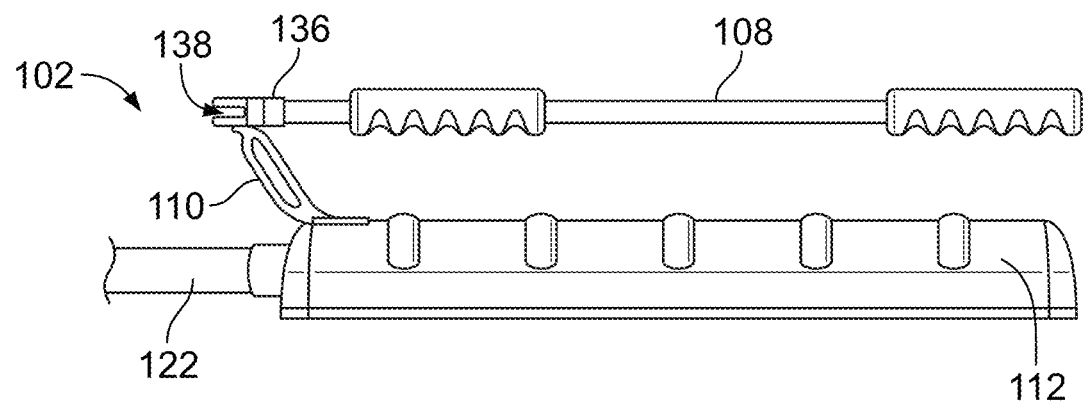
FIG. 4 illustrates a perspective lateral view of the wand assembly of FIG. 2.

FIG. 3 illustrates a perspective rear view of the wand assembly 102 of FIG. 2. FIG. 4 illustrates a perspective lateral view of the wand assembly 102 of FIG. 2. Referring to FIGS. 3 and 4, the handle 108 may pivotally couple to the coupler 110 through a bearing 136 having a pivot axle 138 that pivotally couples the handle 108 to the coupler 110. The handle 108 may further be configured to linearly translate into and out of the bearing 136. For example, the handle 108 may be configured to telescope in and out. Optionally, or alternatively, in at least one embodiment, the handle 108 may include a telescoping body that allows the handle 108 to outwardly extend and inwardly recede.

Figure 5:
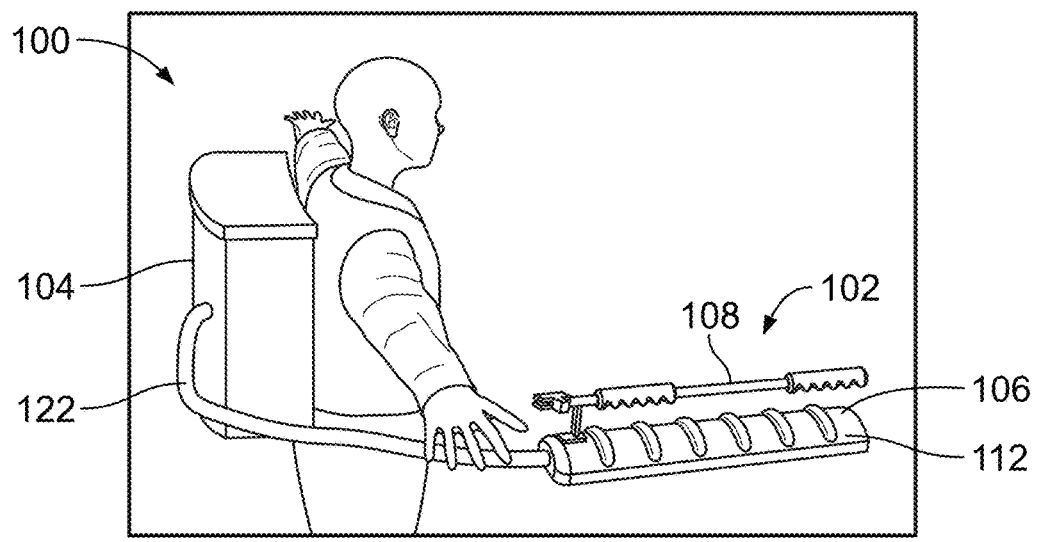
FIG. 5 illustrates a perspective view of the portable sanitizing system in a compact deployed position, according to an embodiment of the present disclosure.

FIG. 5 illustrates a perspective view of the portable sanitizing system 100 in a compact deployed position, according to an embodiment of the present disclosure. The wand assembly 102 is removed from the backpack assembly 104 (as shown in FIG. 1) into the compact deployed position, as shown in FIG. 5. The hose 122 connects the wand assembly 102 to the backpack assembly 104. In the compact deployed position, the sanitizing head 106 is fully retracted in relation to the handle 108.

Figure 6:
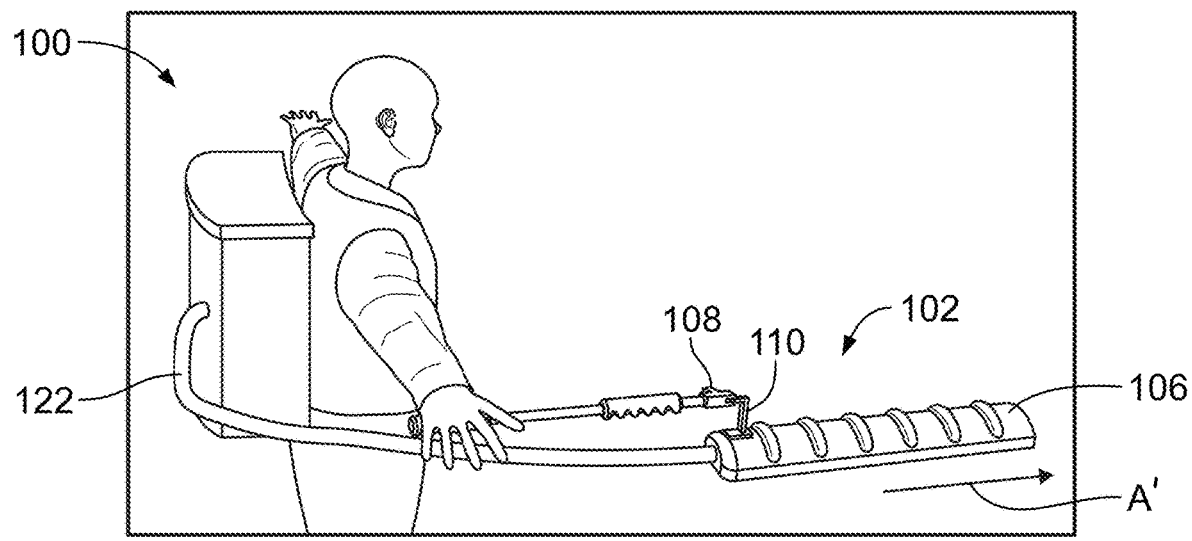
FIG. 6 illustrates a perspective view of the portable sanitizing system having a sanitizing head in an extended position, according to an embodiment of the present disclosure.

FIG. 6 illustrates a perspective view of the portable sanitizing system 100 having the sanitizing head 106 in an extended position, according to an embodiment of the present disclosure. In order to extend the sanitizing head 106 relative to the handle 108, the sanitizing head 106 is outwardly slid relative to the handle 108 in the direction of arrow A' (or the handle 108 is rearwardly slid relative to the sanitizing head 106). As noted, the sanitizing head 106 is able to linearly translate in the direction of arrow A' relative to the handle 108 via the coupler 110. The outward extension of the sanitizing head 106, as shown in FIG. 6, allows for the portable sanitizing system 100 to easily reach distant areas. Alternatively, the sanitizing head 106 may not linearly translate relative to the handle 108.

Figure 7:
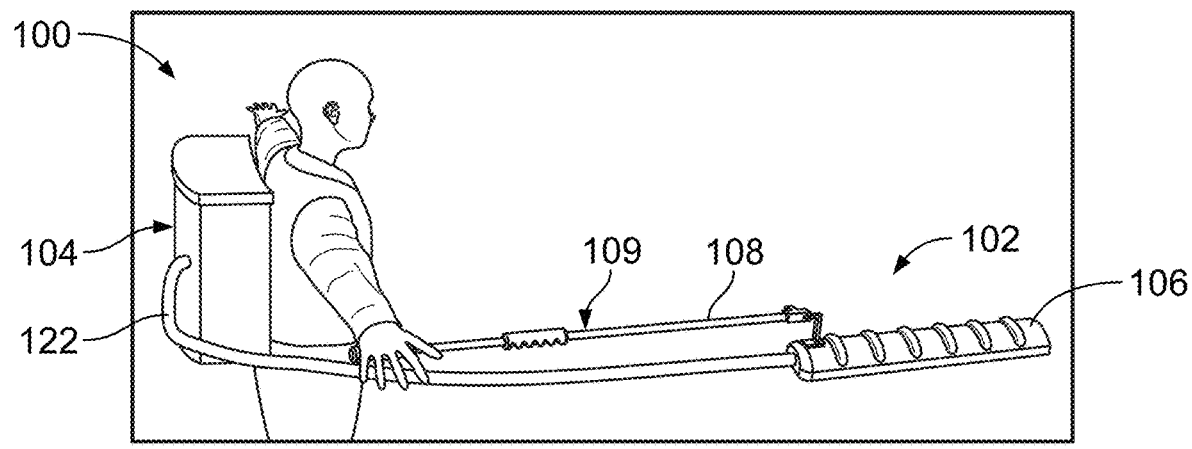
FIG. 7 illustrates a perspective view of the portable sanitizing system having the sanitizing head in an extended position and a handle in an extended position, according to an embodiment of the present disclosure.

FIG. 7 illustrates a perspective view of the portable sanitizing system 100 having the sanitizing head 106 in an extended position and the handle 108 in an extended position, according to an embodiment of the present disclosure. To reach even further, the handle 108 may be configured to linearly translate, such as through a telescoping portion, to allow the sanitizing head 106 to reach further outwardly. Alternatively, the handle 108 may not be configured to extend and retract.

In at least one embodiment, the handle 108 may include a lock 109. The lock 109 is configured to be selectively operated to secure the handle 108 into a desired extended (or retracted) position.

Figure 8:
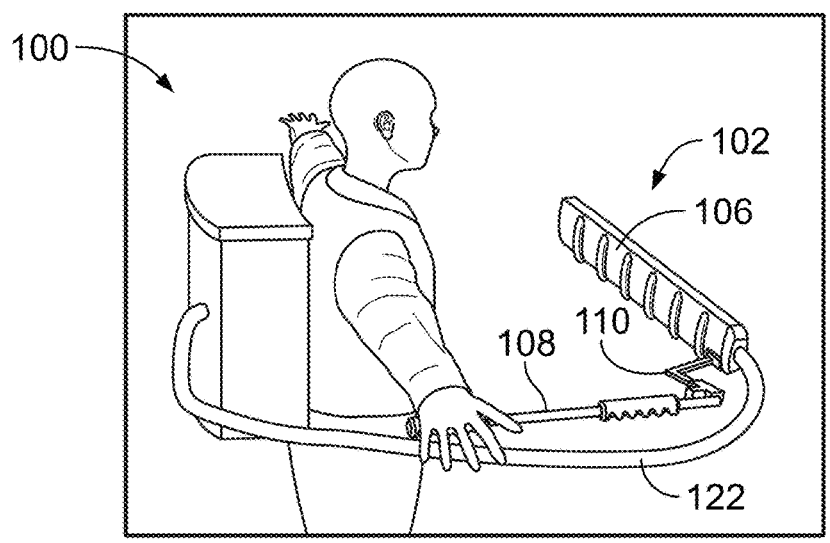
FIG. 8 illustrates a perspective view of the portable sanitizing system having the sanitizing head rotated in relation to the handle, according to an embodiment of the present disclosure.

FIG. 8 illustrates a perspective view of the portable sanitizing system 100 having the sanitizing head 106 rotated in relation to the handle 108, according to an embodiment of the present disclosure. As noted, the sanitizing head 106 is configured to rotate relative to the handle 108 via the coupler 110. Rotating the sanitizing head 106 relative to the handle 108 allows the sanitizing head 106 to be moved to a desired position, and sweep or otherwise reach into areas that would otherwise be difficult to reach if the sanitizing head 106 was rigidly fixed to the handle 108. Alternatively, the sanitizing head 106 may not be rotatable relative to the handle 108.

Figure 9:
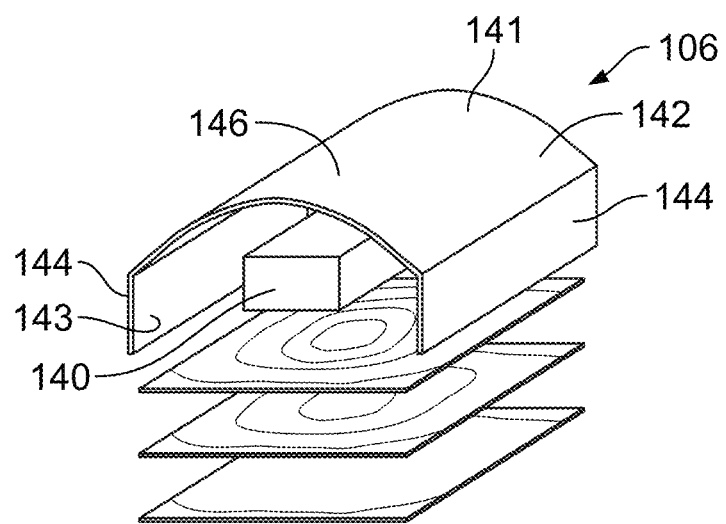
FIG. 9 illustrates a perspective end view of a UV lamp and a reflector of the sanitizing head, according to an embodiment of the present disclosure.

FIG. 9 illustrates a perspective end view of a UV lamp 140 and a reflector 142 of the sanitizing head 106, according to an embodiment of the present disclosure. The UV lamp 140 and the reflector 142 are secured within the shroud 112 (shown in FIG. 2, for example) of the sanitizing head 106. In at least one embodiment, the reflector 142 is secured to an underside 141 of the shroud 112, such as through one or more adhesives. As another example, the reflector 142 is an integral part of the shroud 112. For example, the reflector 142 may be or otherwise provide the underside 141 of the shroud 112. The reflector 142 provides a reflective surface 143 (such as formed of Teflon, a mirrored surface, and/or the like) that is configured to outwardly reflect UV light emitted by the UV lamp 140. In at least one example, shroud 112 may be or include a shell formed of fiberglass, and the reflector 142 may be formed of Teflon that provides a 98% reflectivity.

The reflector 142 may extend along an entire length of the underside 141 of the shroud 112. Optionally, the reflector 142 may extend along less than an entire length of the underside 141 of the shroud 112.

The UV lamp 140 may extend along an entire length (or along substantially the entire length, such as between the ends 116 and 118). The UV lamp 140 is secured to the reflector 142 and/or the shroud 112 through one or more brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200 nm-230 nm. In at least one embodiment, the UV lamp 140 is configured to emit UV light having a wavelength of 222 nm. For example, the UV lamp 140 may be or include a 300 W bulb that is configured to emit UV light having a wavelength of 222 nm. In at least one other embodiment, the UV lamp 140 is configured to emit UV light in the UVC spectrum, such as at a wavelength between 230 nm-280 nm.

As shown, the reflector 142 includes flat, upright side walls 144 connected together through an upper curved wall 146. The upper curved wall 146 may be bowed outwardly away from the UV lamp 140. For example, the upper curved wall 146 may have a parabolic cross-section and/or profile.

It has been found that the straight, linear side walls 144 provide desired reflection and/or focusing of UV light emitted from the UV lamp 140 toward and onto a desired location. Alternatively, the side walls 144 may not be linear and flat.

Figure 10:
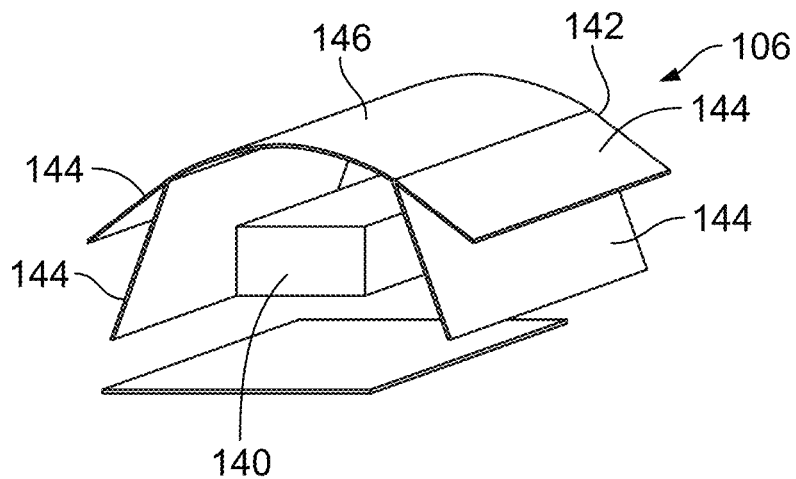
FIG. 10 illustrates a perspective end view of a UV lamp and a reflector of the sanitizing head, according to an embodiment of the present disclosure.

FIG. 10 illustrates a perspective end view of the UV lamp 140 and a reflector 142 of the sanitizing head, according to an embodiment of the present disclosure. The reflector 142 shown in FIG. 10 is similar to the reflector 142 shown in FIG. 9, except that the side walls 144 may outwardly cant from the upper curved wall 146.

Figure 11:
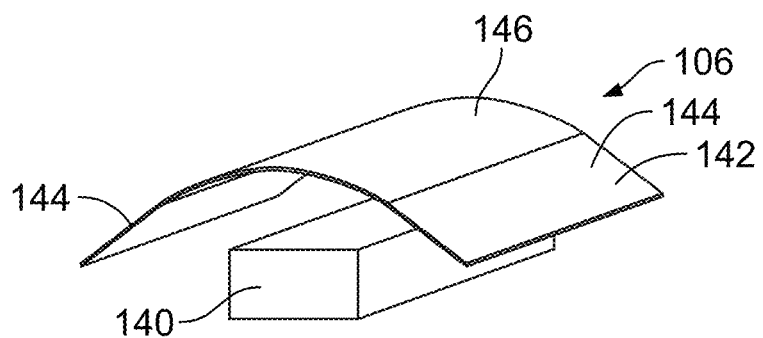
FIG. 11 illustrates a perspective end view of a UV lamp and a reflector of the sanitizing head, according to an embodiment of the present disclosure.

FIG. 11 illustrates a perspective end view of the UV lamp 140 and the reflector 142 of the sanitizing head, according to an embodiment of the present disclosure. In this embodiment, the side walls 144 may be curved according to the curvature of the upper curved wall 146.

Figure 12:
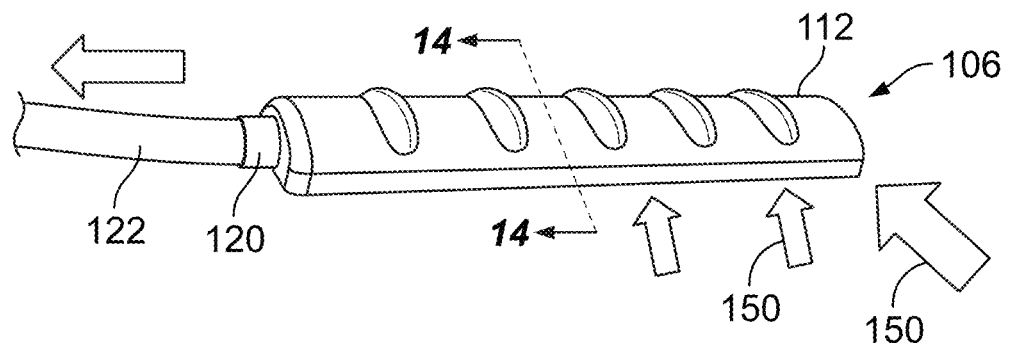
FIG. 12 illustrates a perspective top view of the sanitizing head.
Figure 13:
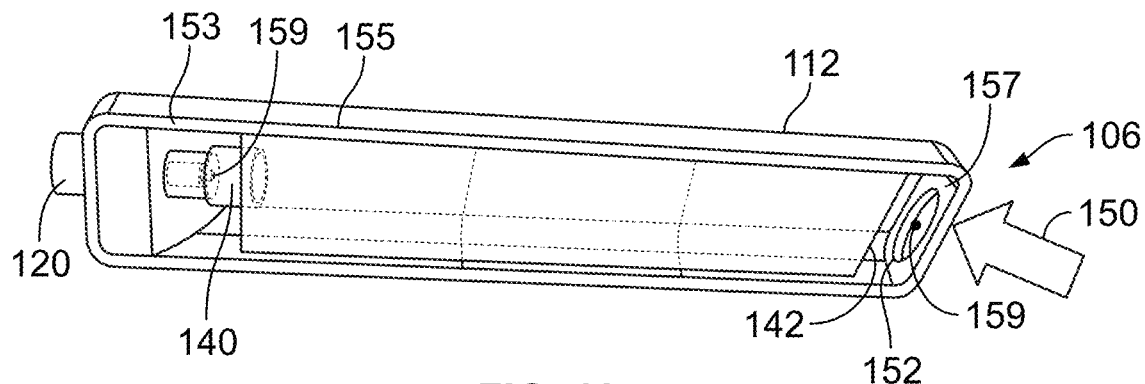
FIG. 13 illustrates a perspective bottom view of the sanitizing head.
Figure 14:
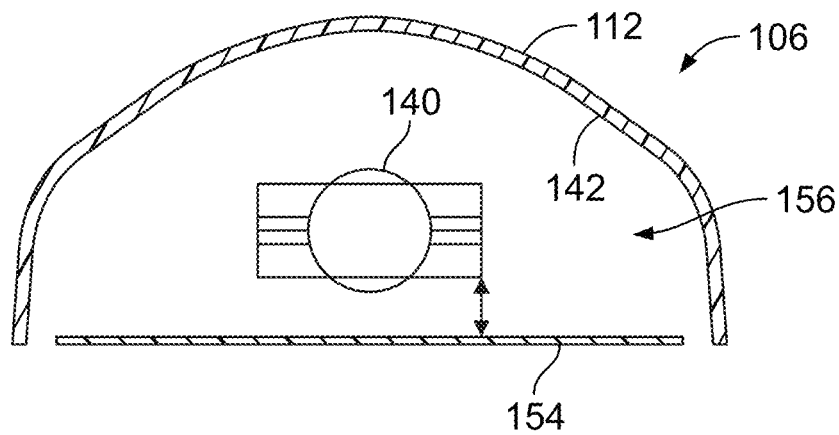
FIG. 14 illustrates an axial cross-sectional view of the sanitizing head through line 14-14 of FIG. 12.

FIG. 12 illustrates a perspective top view of the sanitizing head 106. FIG. 13 illustrates a perspective bottom view of the sanitizing head 106. FIG. 14 illustrates an axial cross-sectional view of the sanitizing head 106 through line 14-14 of FIG. 12. Referring to FIGS. 12-14, air 150 is configured to be drawn into the sanitizing head 106 through one or more openings 152 (or simply an open chamber) of the shroud 112. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The air 150 passes into the port 120 and into the hose 122, such as within an air tube within the hose 122. The air 150 not only cools the UV lamp 140, but also removes ozone, which may be generated by operation of the UV lamp 140, within the shroud 112. The air 150 may be drawn to an air filter, such as an activated carbon filter, within the backpack assembly 104.

In at least one embodiment, the portable sanitizing system 100 may also include an alternative ozone mitigation system. As an example, the ozone mitigation system may be disposed in the shroud 112 or another portion of the system, and may include an inert gas bath, or a face inert gas system, such as in U.S. Pat. No. 10,232,954.

Referring to FIG. 13, in particular, a bumper 153 may be secured to an exposed lower circumferential edge 155 of the shroud 112. The bumper 153 may be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage.

The openings 152 may be spaced around the lower surface of the shroud 112 such that they do not provide a direct view of the UV lamp 140. For example, the openings 152 may be positioned underneath portions that are spaced apart from the UV lamp 140.

Referring to FIG. 14, in particular, the sanitizing head 106 may include a cover plate 154 below the UV lamp 140. The cover plate 154 may be formed of glass, for example, and may be configured to filter UV light emitted by the UV lamp 140. The UV lamp 140 may be secured within an interior chamber 156 defined between the reflector 142 and the cover plate 154. In at least one embodiment, the cover plate 154 is or otherwise includes a far UV band pass filter. For example, the cover plate 154 may be a 222 nm band pass filter that filters UV light emitted by the UV lamp 140 to a 222 nm wavelength. As such, UV light that is emitted from the sanitizing head 106 may be emitted at a wavelength of 222 nm.

Referring to FIGS. 13 and 14, a rim 157 (such as a 0.020" thick Titanium rim) may connect the cover plate 154 to the shroud 112. The rim 157 may distribute impact loads therethrough and/or therearound.

In at least one embodiment, ranging light emitting diodes (LEDs) 159 may be disposed proximate to ends of the UV lamp 140. The ranging LEDs 159 may be used to determine a desired range to a structure that is to be sanitized, for example. In at least one embodiment, the ranging LEDs 159 may be disposed on or within the rim 157 and/or the cover plate 154.

Figure 15:
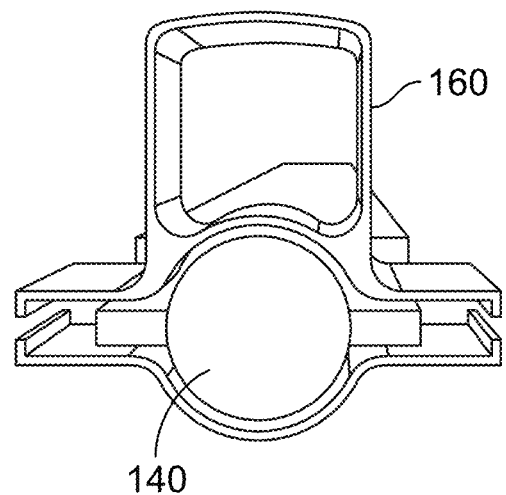
FIG. 15 illustrates a perspective end view of the UV lamp secured to a mounting bracket, according to an embodiment of the present disclosure.

FIG. 15 illustrates a perspective end view of the UV lamp 140 secured to a mounting bracket or clamp 160, according to an embodiment of the present disclosure. Each end of the UV lamp 140 may be coupled to mounting bracket or clamp 160, which secures the UV lamp 140 to the shroud 112 (shown in FIGS. 12-14). A buffer, such as a thin (for example, 0.040") sheet of silicon may be disposed between the end of the UV lamp 140 and the bracket 160. Optionally, the UV lamp 140 may be secured to the shroud 112 through brackets or clamps that differ in size and shape than shown. As another example, the UV lamp 140 may be secured to the shroud 112 through adhesives, fasteners, and/or the like.

Figure 16:
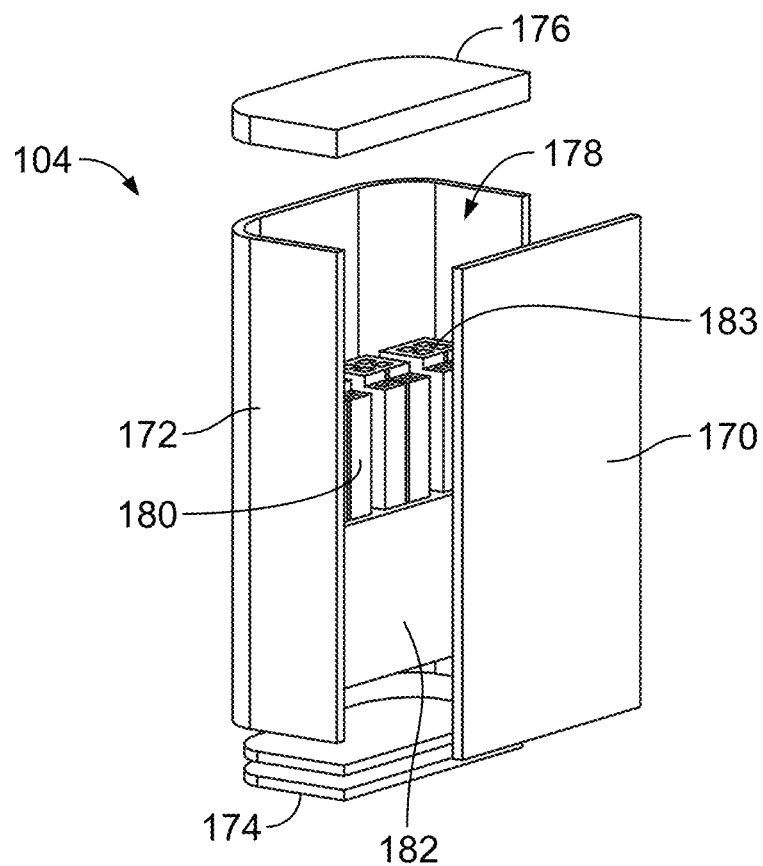
FIG. 16 illustrates a perspective exploded view of a backpack assembly, according to an embodiment of the present disclosure.

FIG. 16 illustrates a perspective exploded view of the backpack assembly 104, according to an embodiment of the present disclosure. The backpack assembly 104 includes a front wall 170 that couples to a rear shell 172, a base 174, and a top cap 176. An internal chamber 178 is defined between the front wall 170, the rear shell 172, the base 174, and the top cap 176. One or more batteries 180, such as rechargeable Lithium batteries, are contained within the internal chamber 178. An air generation sub-system 182 is also contained within the internal chamber 178. The air generation sub-system 182 is in fluid communication with an air tube within the hose 122 (shown in FIG. 2, for example). The air generation sub-system 182 may include an airflow device, such as a vacuum generator, an air blower, and/or the like. The airflow device is configured to generate airflow to cool the UV lamp, draw air from the sanitizing head 106 into the backpack assembly 104 and out through an exhaust, draw or otherwise remove generated ozone away from the shroud 112, and/or the like.

One or more air filters 183, such as carbon filters, are within the backpack assembly 104. The air filters 183 are in communication with the air tube or other such delivery duct or line that routes air through the hose 122 and into the backpack assembly 104. The air filters 183 are configured to filter the air that is drawn into the backpack assembly 104 from the shroud 112. For example, the air filters 183 may be configured to remove, deactivate, or otherwise neutralize ozone.

The batteries 180 and/or a power supply or controller within the backpack assembly 104 provides operating power for the UV lamp 140 of the sanitizing head 106 (shown in FIG. 2, for example). The top cap 176 may be removably coupled to the front wall 170 and the rear shell 172. The top cap 176 may be removed to provide access to the batteries 180 (such as to remove and/or recharge the batteries), for example. Additional space may be provided within the backpack assembly 104 for storage of supplies, additional batteries, additional components, and/or the like. In at least one embodiment, the front wall 170, the rear shell 172, the base 174, and the top cap 176 may be formed of fiberglass epoxy.

Figure 17:
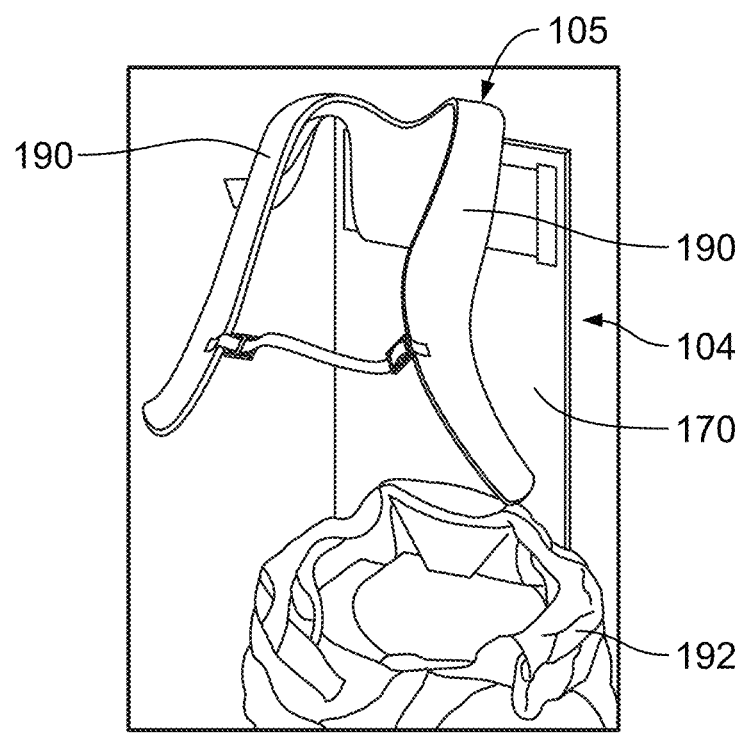
FIG. 17 illustrates a perspective front view of a harness coupled to a backpack assembly, according to an embodiment of the present disclosure.

FIG. 17 illustrates a perspective front view of the harness 105 coupled to the backpack assembly 104, according to an embodiment of the present disclosure. The harness 105 may include shoulder straps 190 and/or a waist or hip belt or strap 192, which allow the individual to comfortably wear the backpack assembly 104.

Referring to FIGS. 1-17, in operation, the individual may walk through an area wearing the backpack assembly 104. When a structure to be sanitized is found, the individual may position grasp the handle 108 and position the sanitizing head 106 as desired, such as by extending and/or rotating the sanitizing head 106 relative to the handle 108. The individual may then engage an activation button on the handle 108, for example, to activate the UV lamp 140 to emit sanitizing UV light onto the structure. As the UV lamp 140 is activated, air 150 is drawn into the shroud 112 to cool the UV lamp 140, and divert any generated ozone into the backpack assembly 104, where it is filtered by the air filters 183.

The extendable wand assembly 102 allows the sanitizing head 106 to reach distant areas, such as over an entire set of three passenger seats, from a row within an internal cabin of a commercial aircraft.

Figure 18:
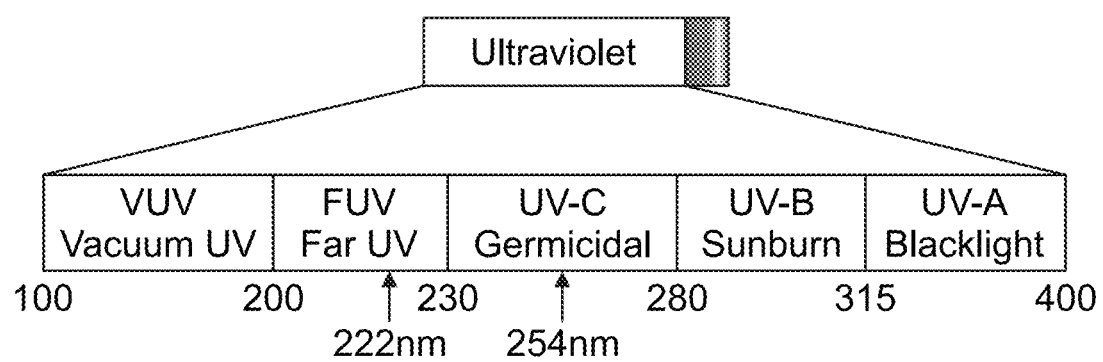
FIG. 18 illustrates an ultraviolet light spectrum.

FIG. 18 illustrates an ultraviolet light spectrum. Referring to FIGS. 1-18, in at least one embodiment, the sanitizing head 106 is configured to emit sanitizing UV light (through operation of the UV lamp 140) within a far UV spectrum, such as between 200 nm to 230 nm. In at least one embodiment, the sanitizing head 106 emits sanitizing UV light having a wavelength of 222 nm.

It has been found that sanitizing UV light having a wavelength of 222 nm kills pathogens (such as viruses and bacteria), instead of inactivating pathogens. In contrast, UVC light at a wavelength of 254 nm inactivates pathogens by interfering with their DNA, resulting in temporary inactivation, but may not kill the pathogens. Instead, the pathogen may be reactivated by exposure to ordinary white light at a reactivation rate of about 10% per hour. As such, UVC light at a wavelength of 254 nm may be ineffective in illuminated areas, such as within an internal cabin of a vehicle. Moreover, UVC light at 254 nm is not recommended for human exposure because it may be able to penetrate human cells.

In contrast, sanitizing UV light having a wavelength of 222 nm is safe for human exposure and kills pathogens. Further, the sanitizing UV light having a wavelength of 222 nm may be emitted at full power within one millisecond or less of the UV lamp 140 being activated (in contrast the UVC light having a wavelength of 254 nm, which may take seconds or even minutes to reach full power).

Figure 19:
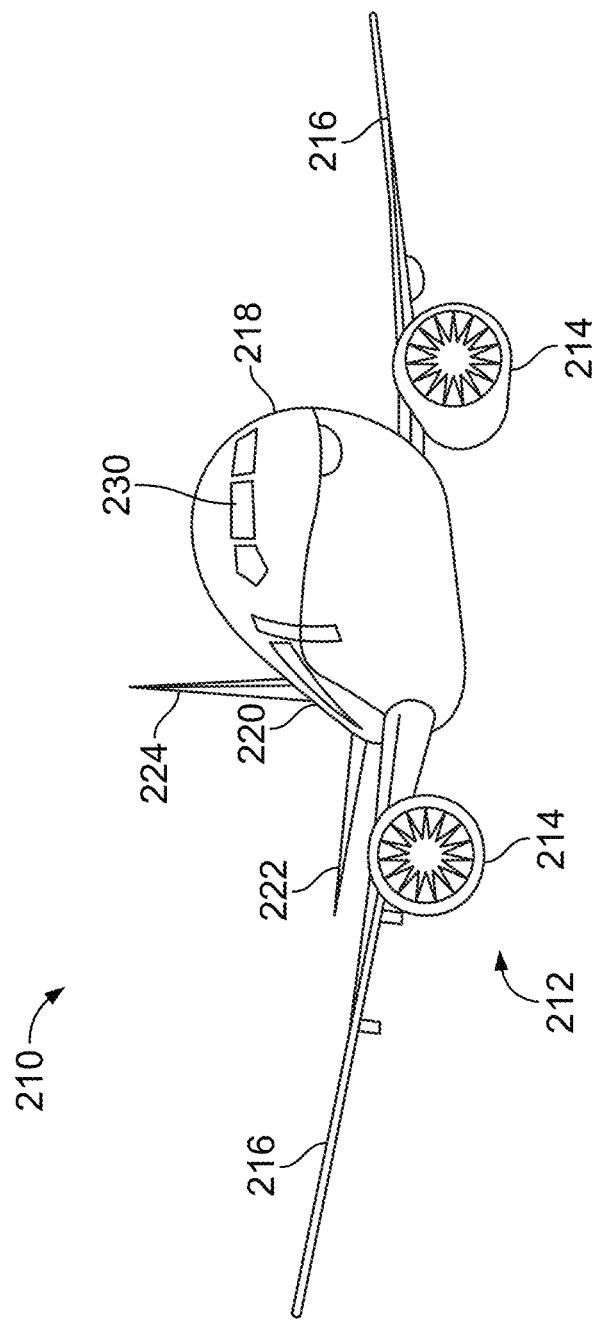
FIG. 19 illustrates a perspective front view of an aircraft, according to an embodiment of the present disclosure.

FIG. 19 illustrates a perspective front view of an aircraft 210, according to an embodiment of the present disclosure. The aircraft 210 includes a propulsion system 212 that includes engines 214, for example. Optionally, the propulsion system 212 may include more engines 14 than shown. The engines 214 are carried by wings 216 of the aircraft 210. In other embodiments, the engines 214 may be carried by a fuselage 218 and/or an empennage 220. The empennage 220 may also support horizontal stabilizers 222 and a vertical stabilizer 224.

The fuselage 218 of the aircraft 210 defines an internal cabin 230, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 230 includes one or more lavatory systems, lavatory units, or lavatories, as described herein.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 20A:
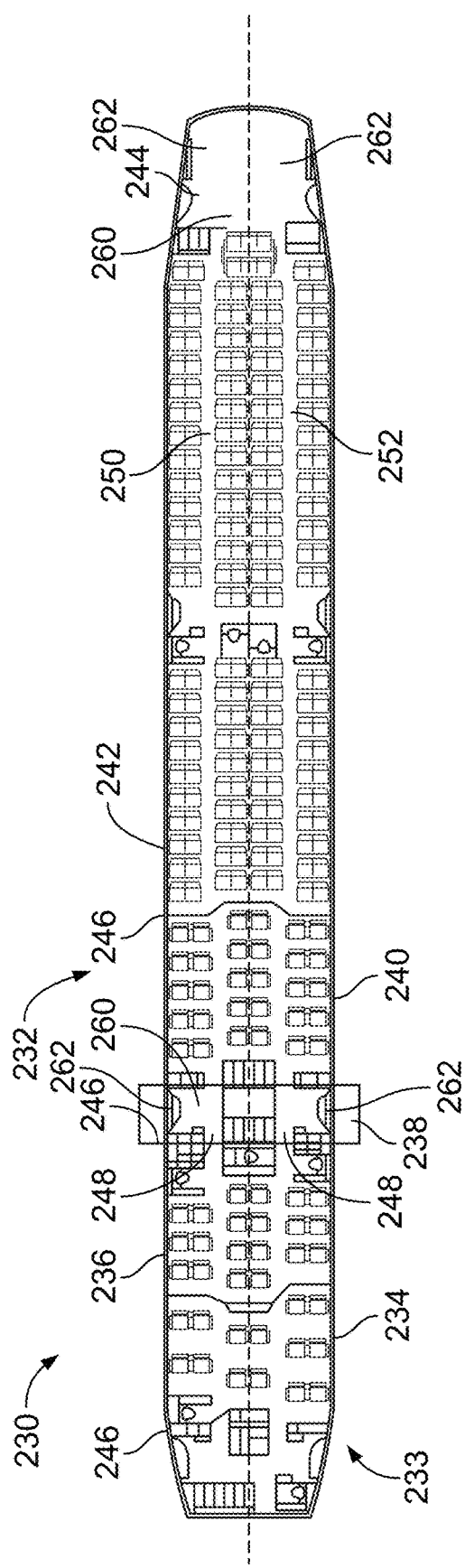
FIG. 20A illustrates a top plan view of an internal cabin of an aircraft, according to an embodiment of the present disclosure.

FIG. 20A illustrates a top plan view of an internal cabin 230 of an aircraft, according to an embodiment of the present disclosure. The internal cabin 230 may be within the fuselage 232 of the aircraft, such as the fuselage 218 of FIG. 19. For example, one or more fuselage walls may define the internal cabin 230. The internal cabin 230 includes multiple sections, including a front section 233, a first class section 234, a business class section 236, a front galley station 238, an expanded economy or coach section 240, a standard economy of coach section 242, and an aft section 244, which may include multiple lavatories and galley stations. It is to be understood that the internal cabin 230 may include more or less sections than shown. For example, the internal cabin 230 may not include a first class section, and may include more or less galley stations than shown. Each of the sections may be separated by a cabin transition area 246, which may include class divider assemblies between aisles 248.

As shown in FIG. 20A, the internal cabin 230 includes two aisles 250 and 252 that lead to the aft section 244. Optionally, the internal cabin 230 may have less or more aisles than shown. For example, the internal cabin 230 may include a single aisle that extends through the center of the internal cabin 230 that leads to the aft section 244.

The aisles 248, 250, and 252 extend to egress paths or door passageways 260. Exit doors 262 are located at ends of the egress paths 260. The egress paths 260 may be perpendicular to the aisles 248, 250, and 252. The internal cabin 230 may include more egress paths 260 at different locations than shown. The portable sanitizing system 100 shown and described with respect to FIGS. 1-18 may be used to sanitize various structures within the internal cabin 230, such as passenger seats, monuments, stowage bin assemblies, components on and within lavatories, galley equipment and components, and/or the like.

Figure 20B:
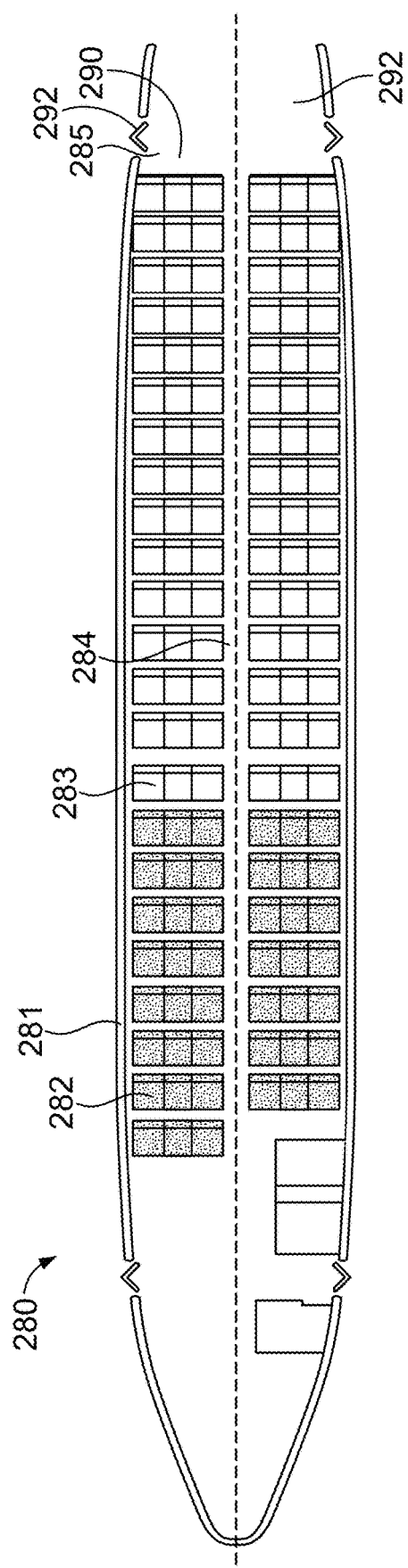
FIG. 20B illustrates a top plan view of an internal cabin of an aircraft, according to an embodiment of the present disclosure.

FIG. 20B illustrates a top plan view of an internal cabin 280 of an aircraft, according to an embodiment of the present disclosure. The internal cabin 280 is an example of the internal cabin 230 shown in FIG. 19. The internal cabin 280 may be within a fuselage 281 of the aircraft. For example, one or more fuselage walls may define the internal cabin 280. The internal cabin 280 includes multiple sections, including a main cabin 282 having passenger seats 283, and an aft section 285 behind the main cabin 282. It is to be understood that the internal cabin 280 may include more or less sections than shown.

The internal cabin 280 may include a single aisle 284 that leads to the aft section 285. The single aisle 284 may extend through the center of the internal cabin 280 that leads to the aft section 285. For example, the single aisle 284 may be coaxially aligned with a central longitudinal plane of the internal cabin 280.

The aisle 284 extends to an egress path or door passageway 290. Exit doors 292 are located at ends of the egress path 290. The egress path 290 may be perpendicular to the aisle 284. The internal cabin 280 may include more egress paths than shown. The portable sanitizing system 100 shown and described with respect to FIGS. 1-18 may be used to sanitize various structures within the internal cabin 230, such as passenger seats, monuments, stowage bin assemblies, components on and within lavatories, galley equipment and components, and/or the like.

Figure 21:
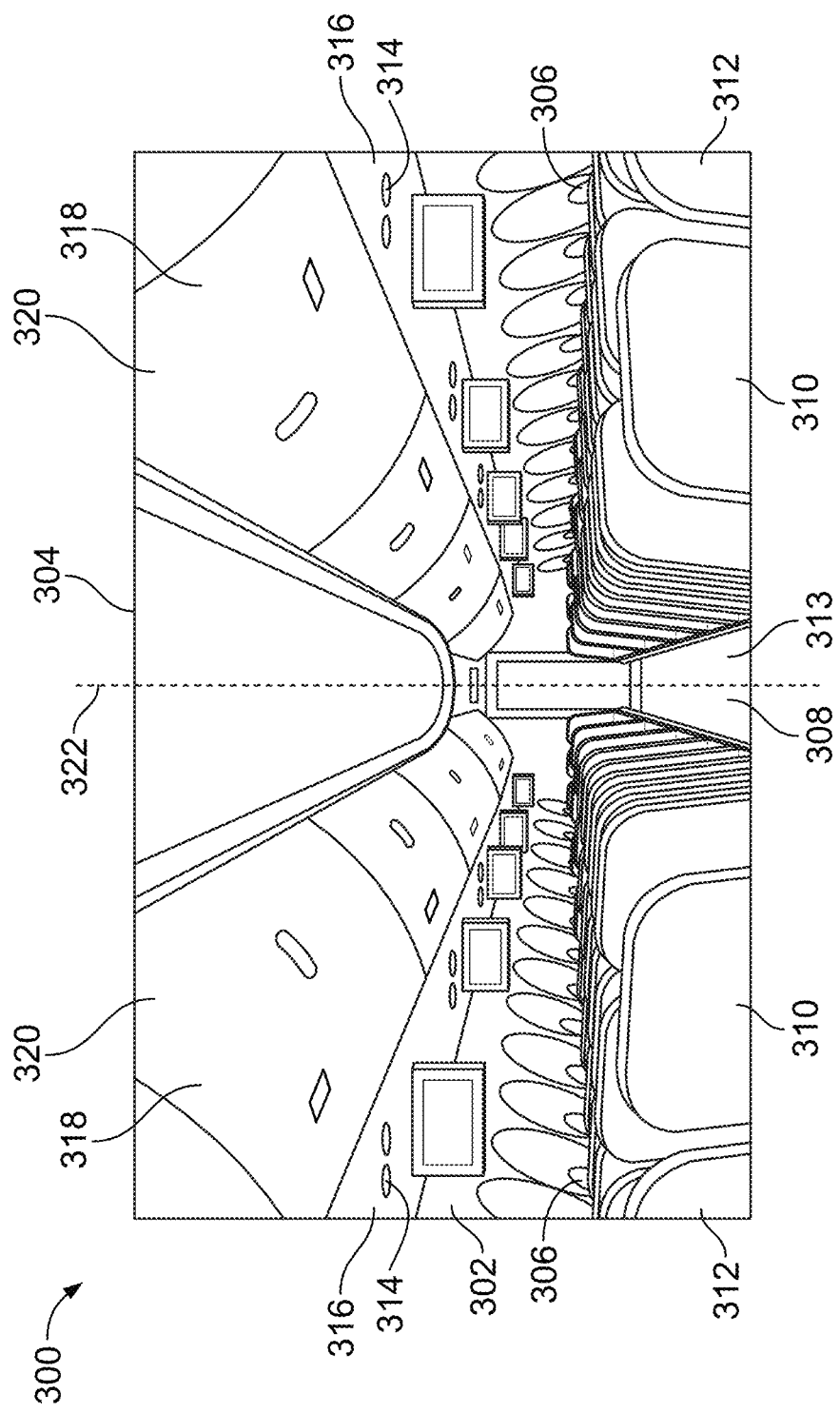
FIG. 21 illustrates a perspective interior view of an internal cabin of an aircraft, according to an embodiment of the present disclosure.

FIG. 21 illustrates a perspective interior view of an internal cabin 300 of an aircraft, according to an embodiment of the present disclosure. The internal cabin 300 includes outboard walls 302 connected to a ceiling 304. Windows 306 may be formed within the outboard walls 302. A floor 308 supports rows of seats 310. As shown in FIG. 21, a row 312 may include two seats 310 on either side of an aisle 313. However, the row 312 may include more or less seats 310 than shown. Additionally, the internal cabin 300 may include more aisles than shown.

Passenger service units (PSUs) 314 are secured between an outboard wall 302 and the ceiling 304 on either side of the aisle 313. The PSUs 314 extend between a front end and rear end of the internal cabin 300. For example, a PSU 314 may be positioned over each seat 310 within a row 312. Each PSU 314 may include a housing 316 that generally contains vents, reading lights, an oxygen bag drop panel, an attendant request button, and other such controls over each seat 310 (or groups of seats) within a row 312.

Overhead stowage bin assemblies 318 are secured to the ceiling 304 and/or the outboard wall 302 above and inboard from the PSU 314 on either side of the aisle 313. The overhead stowage bin assemblies 318 are secured over the seats 310. The overhead stowage bin assemblies 318 extend between the front and rear end of the internal cabin 300. Each stowage bin assembly 318 may include a pivot bin or bucket 320 pivotally secured to a strongback (hidden from view in FIG. 21). The overhead stowage bin assemblies 318 may be positioned above and inboard from lower surfaces of the PSUs 314. The overhead stowage bin assemblies 318 are configured to be pivoted open in order to receive passenger carry-on baggage and personal items, for example.

As used herein, the term "outboard" means a position that is further away from a central longitudinal plane 322 of the internal cabin 300 as compared to another component. The term "inboard" means a position that is closer to the central longitudinal plane 322 of the internal cabin 300 as compared to another component. For example, a lower surface of a PSU 314 may be outboard in relation to a stowage bin assembly 318.

The portable sanitizing system 100 shown and described with respect to FIGS. 1-18 may be used to sanitize various structures shown within the internal cabin 300.

When not in use, the portable sanitizing system 100 may be stored within a closet, galley cart bay, or galley cart, such as within the internal cabin of the vehicle.

Figure 22:
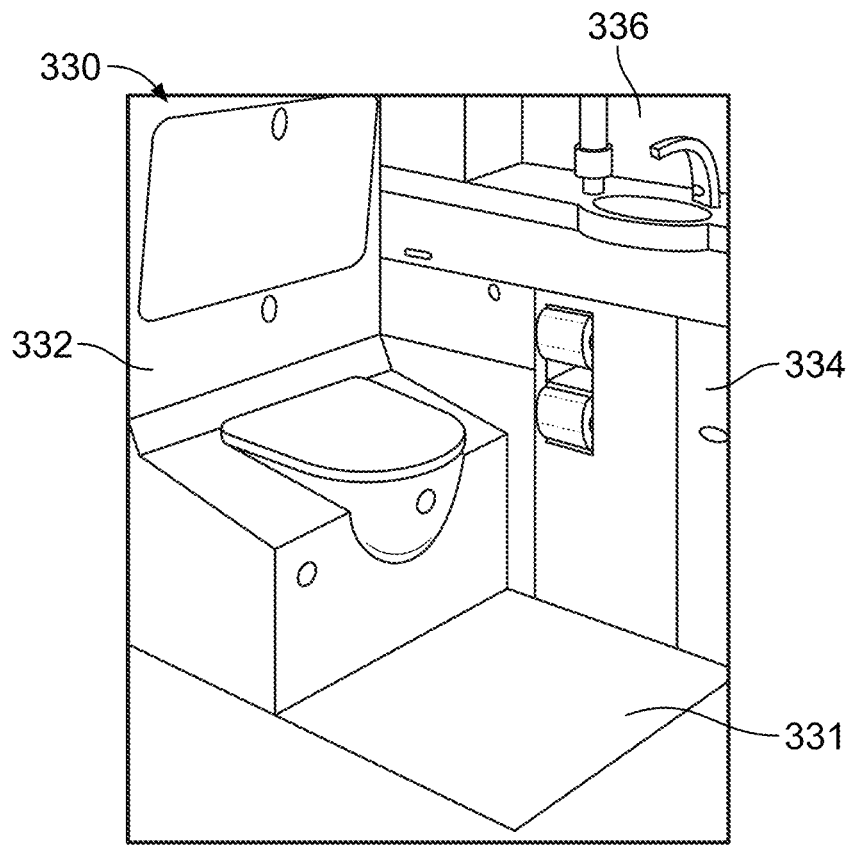
FIG. 22 illustrates a perspective internal view of a lavatory within an internal cabin of an aircraft.

FIG. 22 illustrates a perspective internal view of a lavatory 330 within an internal cabin of a vehicle, such as any of the internal cabins described herein. The lavatory 330 is an example of an enclosed space, monument or chamber, such as within the internal cabin a vehicle. The lavatory 330 may be onboard an aircraft, as described above. Optionally, the lavatory 330 may be onboard various other vehicles. In other embodiments, the lavatory 330 may be within a fixed structure, such as a commercial or residential building. The lavatory 330 includes a base floor 331 that supports a toilet 332, cabinets 334, and a sink 336 or wash basin. The lavatory 330 may be arranged differently than shown. The lavatory 330 may include more or less components than shown. The portable sanitizing system 100 shown and described with respect to FIGS. 1-18 may be used to sanitize the various structures, components, and surfaces within the lavatory 330.

Figure 23:
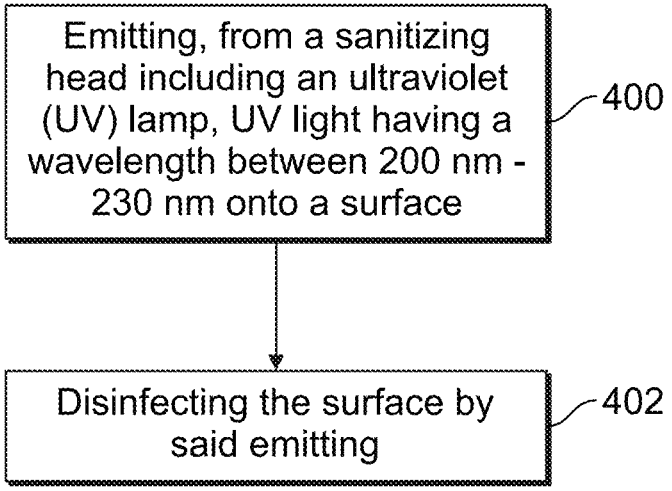
FIG. 23 illustrates a flow chart of a portable sanitizing method, according to an embodiment of the present disclosure.

FIG. 23 illustrates a flow chart of a portable sanitizing method, according to an embodiment of the present disclosure. The method includes emitting (400), from a sanitizing head including an ultraviolet (UV) lamp, UV light having a wavelength between 200 nm-230 nm onto a surface; and disinfecting (402) the surface by said emitting (400). In at least one embodiment, said emitting (400) includes emitting the UV light having a wavelength of 222 nm.

In at least embodiment, the portable sanitizing method further includes moveably coupling a handle to the sanitizing head. For example, said moveably coupling includes one or both of linearly translating or swiveling the sanitizing head in relation to the handle.

In at least one embodiment, the portable sanitizing method includes coupling a backpack assembly to the sanitizing head through a hose.

Referring to FIGS. 1-23, the portable sanitizing system 100 can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the portable sanitizing system 100 is used to augment a cleaning process, such as after manual cleaning.

As described herein, embodiments of the present disclosure provide systems and a methods for efficiently sterilizing surfaces, components, structures, and/or the like within an internal cabin of a vehicle. Further, embodiments of the present disclosure provide compact, easy-to-use, and safe systems and methods for using UV light to sterilize surfaces within an internal cabin.

Figure 24:
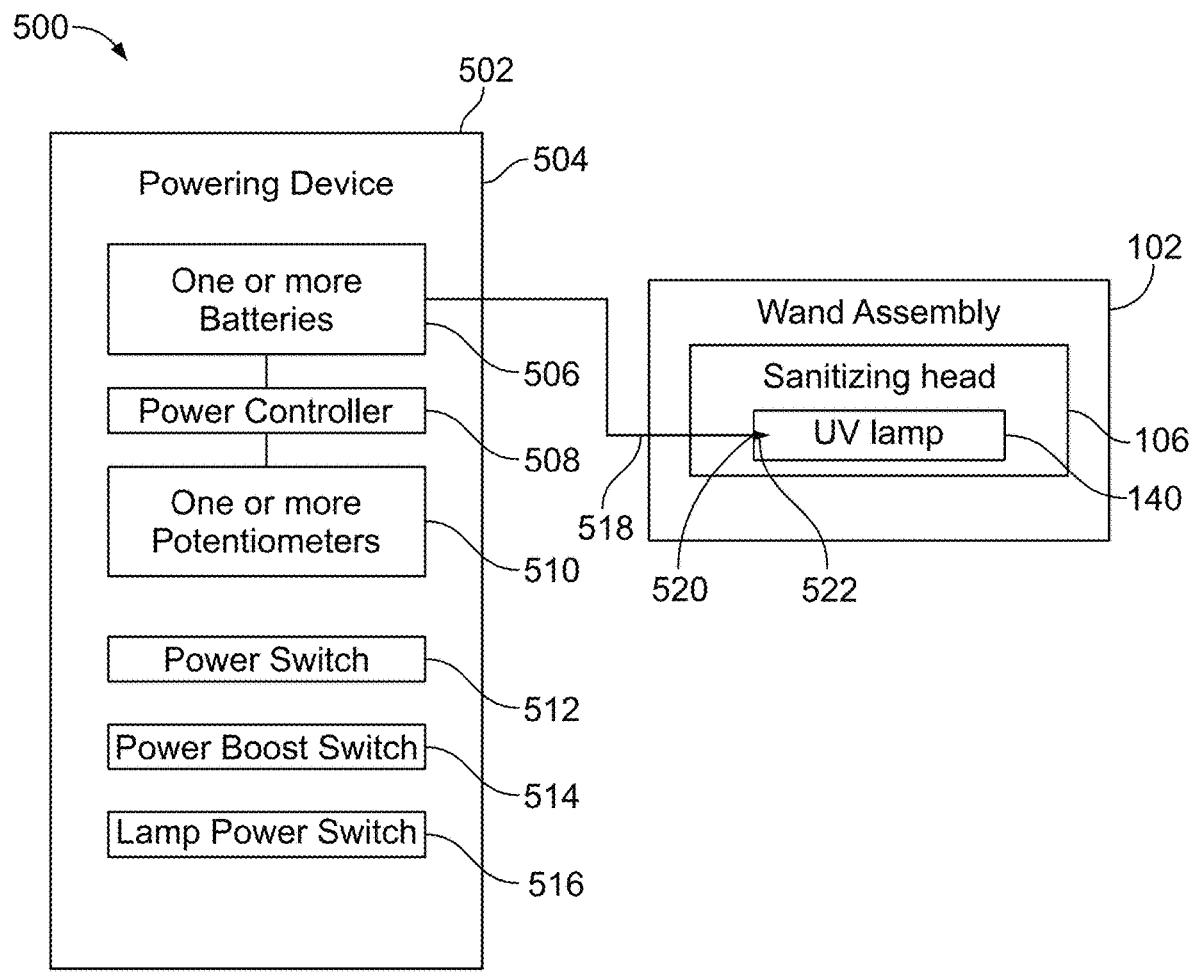
FIG. 24 illustrates a schematic block diagram of a system for providing power to an ultraviolet lamp of a wand assembly, according to an embodiment of the present disclosure.

FIG. 24 illustrates a schematic block diagram of a system 500 for providing power to a UV lamp 140 of a wand assembly 102, according to an embodiment of the present disclosure. In at least one embodiment, the UV lamp 140 is within a sanitizing head 106 of the wand assembly 102. The wand assembly 102 may or may not include a handle. The handle may or may not be moveable in relation to the sanitizing head 106.

Figure 25:
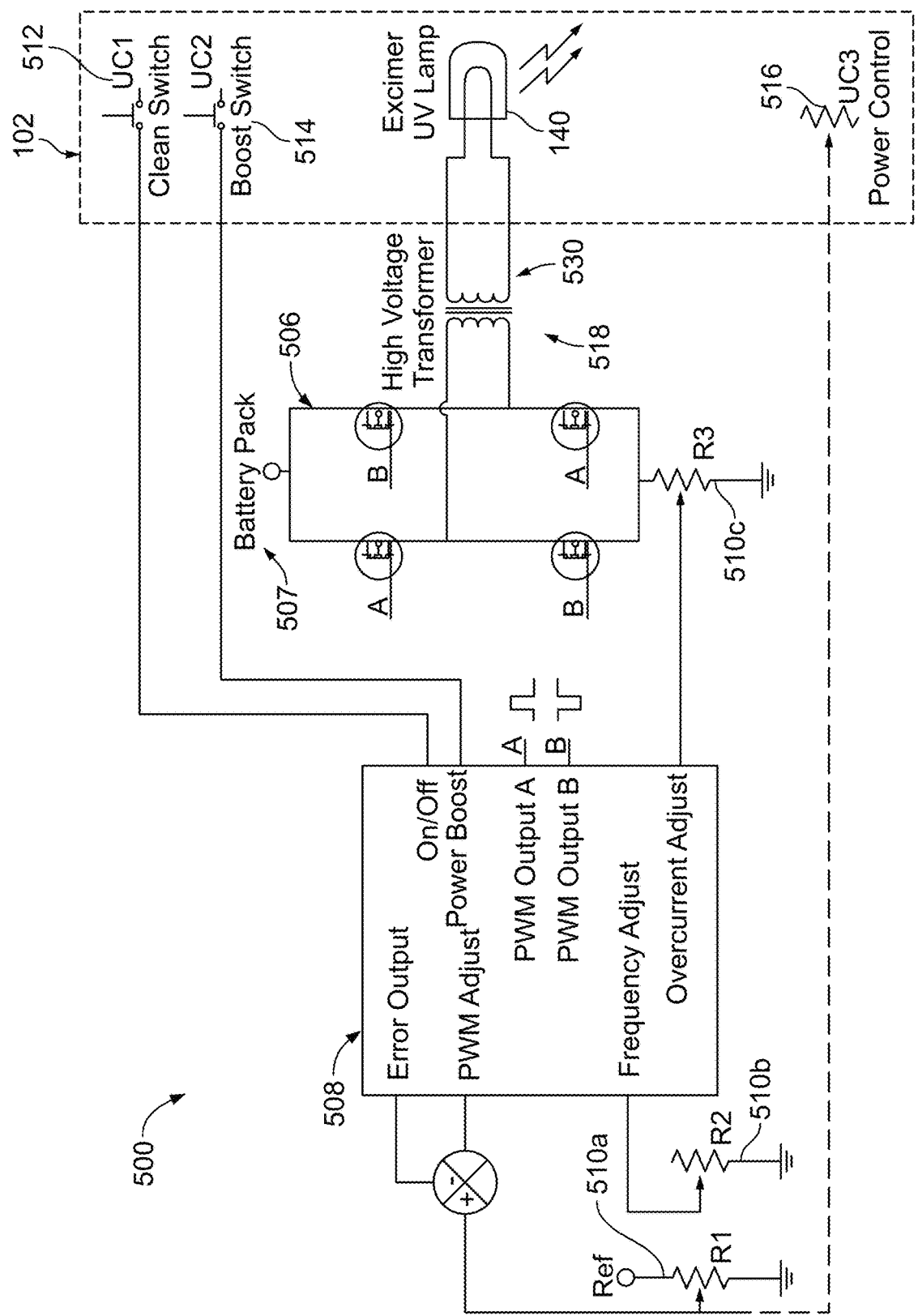
FIG. 25 illustrates a schematic diagram of a system for providing power to an ultraviolet lamp of a wand assembly, according to an embodiment of the present disclosure.

In at least one embodiment, the UV lamp 140 is an excimer lamp (also known as a dielectric barrier discharge (DBD) lamp). Excimer lamps include a noble gas and a halogen gas, and the interaction of these gases emits light in the UV wavelength, such as the far UV range. A high frequency alternating current (AC) power source is used to excite the gases. In at least one embodiment, the high frequency AC power source may be a bridge circuit, which can vary the pulse width to achieve stable output and/or vary the frequency to achieve a stable voltage and/or power output. An example of the circuitry that can be used to excite an excimer lamp is shown in FIG. 25, and described below. The construction of the excimer lamp relies on the capacitance of dielectric barrier(s) to limit high frequency current versus having a short circuit. This capacitance may cause high frequency resonances. The resonances of the UV excimer lamp may be utilized with the drive circuitry of the portable powering device.

As stated above, the portable powering device according to the embodiments herein can also be used to power a metal vapor plasma UV lamp (e.g., non-excimer). Such metal vapor lamps can include mercury vapor, sodium vapor, and/or the like, and applies a current through a conducting metal vapor plasma to produce UV light. The current utilized in metal vapor lamps can be AC or DC and have a wide range of frequencies.

The UV lamp 140 is configured to emit UV light having a wavelength of 222 nm. Optionally, the UV lamp 140 may be configured to emit UV light having a different wavelength. For example, the UV lamp 140 may be configured to emit UV light having a wavelength between 220 nm and 230 nm. In at least one other embodiment, the UV lamp 140 may be configured to emit UV light in the UVC spectrum.

The system 500 includes a powering device 502 that is configured to provide power to the UV lamp 140. The powering device 502 includes a housing 504. The powering device 502 may be contained within the backpack assembly 104 shown in FIGS. 16 and 17. As an example, the powering device 502 may include or replace the batteries 180. In at least one other embodiment, the powering device 502 is separate and distinct from the backpack assembly 104. For example, the powering device 502 is a portable device that is configured to selectively couple to and decouple from the wand assembly 102. In at least one embodiment, the powering device 502 may be a handheld device.

The housing 504 of the powering device 502 includes one or more batteries 506 and a power controller 508, which includes or is otherwise coupled to one or more potentiometers 510. The power controller 508 is coupled to the batteries 506, such as through one or more wired or wireless connections. The one or more batteries 506 are configured to provide power to the UV lamp 140. The power controller 508 is configured to control one or more aspects of the power delivered from the batteries 506 to the UV lamp 140.

The powering device 502 may also include a plurality of switches on or within the housing 504. For example, the powering device 502 includes a power switch 512, a power boost switch 514, and/or a lamp power switch 516. Optionally, the power switch 512, the power boost switch 514, and the lamp power switch 516 may be on or within the wand assembly 102.

A coupler 518 extends from the batteries 506 and is configured to connect to the UV lamp 140. For example, the coupler 518 may be at least one lead having an output end 520 that connects to a power input 522 of the UV lamp 140. The at least one lead may be one or more insulated wires, metal bars, circuit boards, and/or the like. In at least one embodiment, the coupler 518 includes multiple insulated lead wires, and the configuration of the lead wires can "tune" the UV lamp 140 for one or more properties, such as for higher power output. For example, the multiple insulated wires may be twisted around each other and/or surrounded by a shield layer, either of which may increase the load capacitance and change the resonance of the UV lamp 140 system. In a non-limiting example, an excimer UV lamp directly connected to the power supply (e.g., via untwisted and/or unshielded electrically conductive elements) may produce 9-10 mW of UV light while drawing 375 W. By adding a shielding layer and/or twisting longer wires that represent the coupler 518, the resonance changes and, as a result, the power draw may increase to 750 W and the UV light output may increase to 20 mW, without adjusting the power supply. As such, the shielding and/or twist of the insulated lead wires can be used to tune the excimer lamp load.

In at least one embodiment, the output end 520 may be a plug that is configured to removably connect to the power input 522. Optionally, the coupler 518 may be a fixed connection (that is, not removably connected) between the UV lamp 140 and the powering device 502. For example, the powering device 502 may be secured to, or otherwise form part of, the wand assembly 102. In at least one embodiment, the powering device 502 may be part of a control panel of the wand assembly 102.

The powering device 502 is configured to provide power to the UV lamp 140, such as an excimer lamp that is configured to emit UV light having a wavelength between 220 nm-230 nm. For example, the batteries 506 and the power controller 508 cooperate to provide power to the UV lamp 140.

The potentiometers 510 are configured to adjust or otherwise control frequency, pulse width modulation, and/or current with respect to the power provided to the UV lamp 140. The power switch 512 may be a push button, for example. The power switch 512 may be engaged by a user to activate the powering device 502 to provide power to the UV lamp 140. The user may selectively engage the power switch 512 to selectively provide power to the UV lamp 140.

In at least one embodiment, the portable powering device 502 includes an on/off switch (such as the power switch), the power boost switch 514, and an optional switch to control UV lamp power switch 516. The power boost switch 514 may be engaged by a user to provide increased or boosted power to the UV lamp through the power controller 508 and/or the batteries 506. The UV lamp power switch 516 may be engaged by the user to adjust power of the UV lamp 140, which is coupled to the powering device 502 through the coupler 518. In at least one embodiment, the one or more potentiometers 510 of the power controller 508 are configured to control nominal output power/efficiency of the powering device 502, adjust pulse width frequency and lamp efficiency, and adjust overcurrent. In at least one embodiment, the power controller 508 is configurable by adjusting the potentiometers 510 to provide maximum or otherwise increased UV light output from the UV lamp 140 with minimal or reduced amount of power.

In at least one embodiment, the powering device 502 provides high voltage power to the UV lamp 140 with adjustable voltage, frequency, pulse width, and transient capabilities. The powering device 502 is able to vary the operating temperature, UV output level, power consumption, and heat dissipation of the UV lamp 140.

As described herein, the powering device 502 is configured to provide power to the UV lamp 140 of a sanitizing system, such as the portable sanitizing system 100 (shown in FIG. 1, for example). The powering device 502 includes the one or more batteries 506 configured to provide power to the UV lamp, and the power controller 508 coupled to the one or more batteries 506. The power controller 508 is configured to control one or more aspects of the power provided from the one or more batteries 506 to the UV lamp 140.

In at least one embodiment, the powering device 502 further includes the one or more potentiometers 510 coupled to the power controller 508. The one or more potentiometers 510 are configured to adjust or otherwise control aspects such as frequency, pulse width modulation, and/or current with respect to the power provided to the UV lamp 140.

In at least one embodiment, the powering device 502 further includes one or more switches 512, 514, and/or 516. In an example, the one or more switches are on or within the housing 504 of the powering device 502. In another example, the one or more switches are on or within the wand assembly 102. As an example, the switches include the power switch 512, the power boost switch 514, and the lamp power switch 516.

In at least one embodiment, the coupler 518 connects the batteries 506 to the UV lamp 140. The coupler 518 may include an insulated wire. The coupler 518 may be configured to removably connect to (for example, selectively connect to an disconnect from) the UV lamp 140.

FIG. 25 illustrates a schematic diagram of the system 500 for providing power to the UV lamp 140 of the wand assembly 102, according to an embodiment of the present disclosure. As shown, the wand assembly 102 may include the power switch 512, the power boost switch 514, and the lamp power switch 516. The system 500 may include more or less switches than shown.

A plurality of batteries 506 may be within a battery pack 507. The batteries 506 may be arranged in series and/or parallel. In at least one embodiment, a transformer 530 is disposed between the batteries 506 and the UV lamp 140. For example, the transformer 530 may be part of the coupler 518, or disposed between the coupler 518 and the batteries 506 or the UV lamp 140. The coupler 518 may include at least one insulated lead wire extending between the transformer 530 and the UV lamp 140. The at least one insulated lead wire may be a twisted pair of wires or a coaxial cable. The coaxial cable includes at least one core conductor, at least one insulation layer, and at least one metallic shielding layer. The at least one insulated lead wire may include at least one metallic shielding layer that surrounds insulation layers and metal cores of the wire(s).

The power controller 508 is coupled to a plurality of potentiometers 510a, 510b, and 510c. The power controller 508 may include or otherwise provide a user interface, such as switches, keys, a touchscreen interface, or the like, that is configured to allow a user to adjust various power settings through the potentiometers 510. The potentiometers 510 are configured to control various power parameters or aspects regarding the power delivered to the UV lamp 140. For example, the potentiometer 510a is configured to adjust or otherwise control a nominal output power/efficiency of the power supplied to the UV lamp 140. The potentiometer 510b is configured to adjust the frequency of the pulse width modulation of the power supplied to the UV lamp 140. The potentiometer 510c is configured to adjust an overcurrent trip point of the power supplied to the UV lamp 140.

As shown, the potentiometers 510a, 510b, and 510c may be outside of the power controller 508. Optionally, the potentiometers 510a, 510b, and 510c may be within the power controller 508, such as mounted to a common circuit board or the like. The system 500 may include more or less potentiometers than shown. For example, the system 500 may include only one or two of the potentiometers 510a, 510b, or 510c. Optionally, the system 500 may include additional potentiometers that are configured to adjust or otherwise control different aspects of the power supplied to the UV lamp 140.

In at least one embodiment, current limit may be adjusted through a potentiometer. Pulse width modulation (PWM) may be adjusted through a potentiometer. Frequency may be adjusted through a potentiometer. Battery input may be through 120V direct current. The battery input may be delivered to one or more field effect transistors (FETs). The power controller 508 in FIG. 25 has both a first PWM output (e.g., Output A) and a second PWM output (e.g., Output B) which provide electric current to the transformer 530. In at least one other embodiment, the power controller 508 has a single power output that connects to the UV lamp 140, instead of the dual PWM output shown in FIG. 25.

The power switch 512 is configured to activate and deactivate the UV lamp 140. That is, the power switch 512 is configured to run the UV lamp 140 on and off The power boost switch 514 may have two different functions. The first function may be to command a temporary power increase. For example, when the power boost switch 514 is engaged, a temporary (for example, 10 seconds or less) power boost is supplied to the UV lamp 140. Additionally, the power boost switch 514 can provide starting aid or assist by increasing the voltage. For example, in cold temperature environments, the UV lamp 140 may require a higher voltage to start the UV lamp 140, so the boost switch 514 can be engaged to provide a voltage increase in cold environments, such as when the ambient temperature is less than 5° C., 0° C., or the like. Optionally, the system 500 may not include the power boost switch 514.

The lamp power switch 516 is configured to control the UV lamp power level or output. For example, the lamp power switch 516 may be engaged to selectively increase or decrease lamp power output. Optionally, the system 500 may not include the lamp power switch 516.

Figure 26:
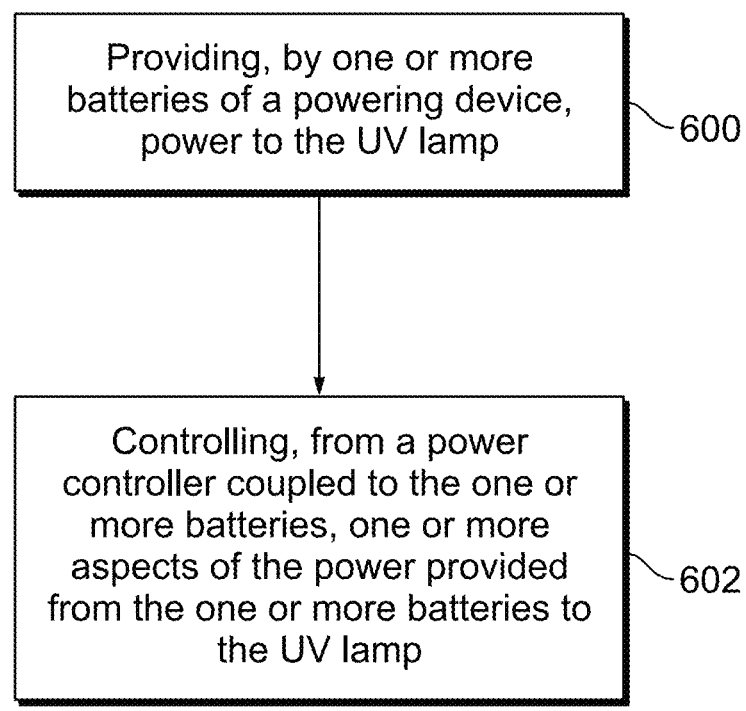
FIG. 26 illustrates a flow chart of a method of providing power to an ultraviolet lamp of a sanitizing system, according to an embodiment of the present disclosure.

FIG. 26 illustrates a flow chart of a method of providing power to an ultraviolet lamp of a sanitizing system, according to an embodiment of the present disclosure. The method includes providing (600), by one or more batteries of a powering device, power to the UV lamp, and controlling (602), from a power controller coupled to the one or more batteries, one or more aspects of the power provided from the one or more batteries to the UV lamp.

In at least one embodiment, the method also includes coupling one or more potentiometers to the power controller. As a further example, the method includes adjusting or otherwise controlling, by the one or more potentiometers, frequency, pulse width modulation, and current with respect to the power provided to the UV lamp.

In at least one embodiment, the method also includes connecting, by a coupler, the one or more batteries to the UV lamp.

In at least one embodiment, the method also includes disposing a transformer between the one or more batteries and the UV lamp.

Figure 27:
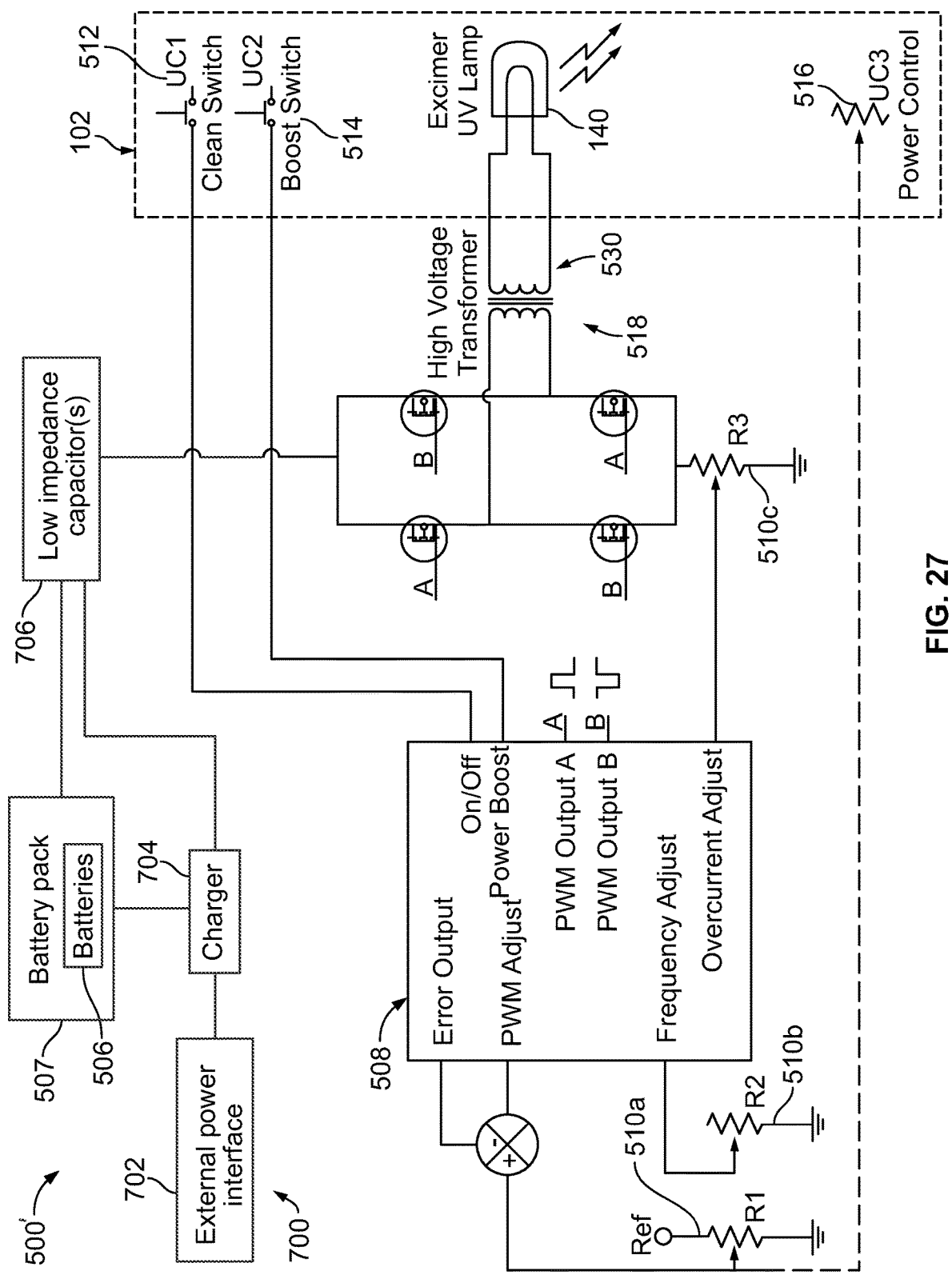
FIG. 27 illustrates a schematic diagram of a system for providing power to an ultraviolet lamp of a wand assembly, in which the system includes a power delivery assembly according to an embodiment of the present disclosure.

FIG. 27 illustrates a schematic diagram of a system 500' for providing power to the UV lamp 140 of the wand assembly 102, in which the system 500' includes a power delivery assembly 700 according to a first embodiment of the present disclosure. The power delivery assembly 700 includes the battery pack 507, one or more low impedance capacitors 706, a charger 704, and an external power interface 702. The charger 704 is electrically connected to both the external power interface 702 and the battery pack 507, and is disposed between the external power interface 702 and the battery pack 507. The battery pack 507 is electrically connected to the one or more capacitors 706, which receive the electric current supplied by the battery pack 507.

The external power interface 702 can include or represent an electrical connector (e.g., a socket, plug, or the like), a power cord, and/or the like, for conveying electrical energy from an external power source to the system 500'. The external power source may be a power circuit integrated into a vehicle or building, a generator, an external battery pack, a solar panel of photovoltaic cells, or the like. The charger 704 is used to selective charge the battery pack 507 based on electrical energy received via the external power interface 702. The charger 704 may be a constant current charger that includes a voltage-limited power factor correction (PFC) circuit and/or a rectifier. In a non-limiting example in which the batteries 506 are lithium ion batteries, the charger 704 may be a constant current, voltage-limited circuit and may provide cell equalization. The charger 704 with the PFC circuit may have the capability to vary the output voltage to the battery pack 507. Optionally, the power boost input may control the PFC output voltage.

In at least one embodiment, the batteries 506 could be charged by an external power source that is connected to the interface 702, even while the system 500' is operating and providing electrical energy to the UV lamp 140. For example, when connected to the external power source, the batteries 506 may be maintained at a designated charge state, such as peak charge, even when operating. Optionally, when power is received from the external power source, the charger 704 may be controlled (e.g., via circuit switching devices) to bypass the battery pack 507 and supply current directly to the capacitor(s) 706. The charger 704 could be configured with a peak power limit, which may be useful in conditions with limited external power supply.

The one or more low impedance capacitors 706 receive the electrical energy from the battery pack 507. The capacitor(s) 706 may temporarily store the energy in order to supply high peak currents that may be required during resonances of the excimer UV lamp 140.

The system 500' may have the capability to operate on AC or DC external power. For example, if the external power is AC, the circuitry within the charger 704, such as a rectifier or the PFC circuit converts the AC to DC before supplying the DC to the battery pack 507. In an alternative embodiment, the power delivery assembly 700 does not include the external power interface 702 and the charger 704. For example, once the batteries 506 are depleted, the batteries 506 may have to be removed and recharged or replaced. Omitting the internal charger 704 can reduce weight and/or manufacturing costs. In another embodiment, the power delivery assembly 700 may retain the external power interface 702 and omit the integrated charger 704, such that the batteries 506 can be selectively charged by connecting the external power interface 702 to an external charger.

Figure 28:
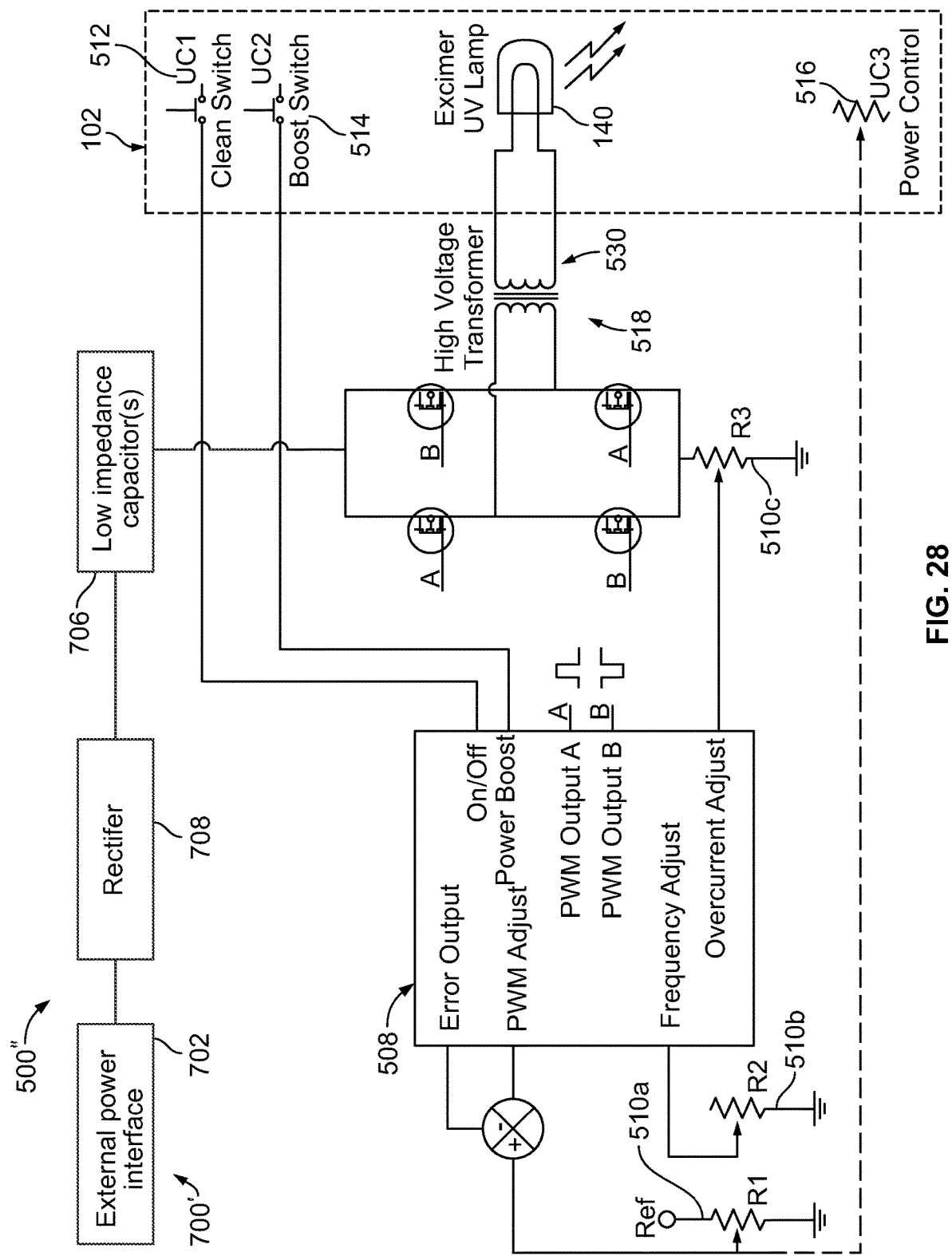
FIG. 28 illustrates a schematic diagram of a system for providing power to an ultraviolet lamp of a wand assembly, in which the system includes a power delivery assembly according to another embodiment of the present disclosure.

FIG. 28 illustrates a schematic diagram of a system 500" for providing power to the UV lamp 140 of the wand assembly 102, in which the system 500" includes a power delivery assembly 700' according to another embodiment of the present disclosure. In the illustrated embodiment, the power delivery assembly 700' lacks the battery pack 507 and charger 704. The power delivery assembly 700' includes the external power interface 702, a rectifier 708, and the one or more low impedance capacitors 706. The rectifier 708 is electrically connected to the interface 702 and the capacitor(s) 706, and is disposed between the interface 702 and the capacitor(s) 706. The rectifier 708 may receive AC electrical energy from the interface 702, convert the AC to DC, and supply the DC to the capacitor(s) 706. The lack of battery pack and charger may reduce weight and/or manufacturing costs. In the illustrated embodiment, the external power interface 702 has to be connected to, and receiving current from, an external power source for the system 500" to operate and power the UV lamp 140.

Further, the disclosure comprises embodiments according to the following clauses:

Clause 1. A powering device configured to provide power to an ultraviolet (UV) lamp of a sanitizing system, the powering device comprising:

a power delivery assembly configured to provide power to the UV lamp; and a power controller coupled to the power delivery assembly, wherein the power controller is configured to control one or more aspects of the power provided from the power delivery assembly to the UV lamp.

Clause 2. The powering device of Clause 1, wherein the UV lamp is within a sanitizing head of a wand assembly.

Clause 3. The powering device of Clause 2, wherein the powering device is within a backpack assembly coupled to the wand assembly.

Clause 4. The powering device of any of Clauses 1-3, wherein the UV lamp is an excimer lamp configured to emit UV light having a wavelength of 222 nm.

Clause 5. The powering device of any of Clauses 1-4, further comprising one or more potentiometers coupled to the power controller and configured to adjust or otherwise control frequency, pulse width modulation, and current with respect to the power provided to the UV lamp.

Clause 6. The powering device of any of Clauses 1-5, wherein the power delivery assembly includes a battery pack and at least one capacitor, the at least one capacitor configured to receive electric current from the battery pack and supply the electric current to a transformer.

Clause 7. The powering device of any of Clauses 1-6, further comprising a power switch, a power boost switch, and a lamp power switch.

Clause 8. The powering device of any of Clauses 1-7, further comprising a coupler that connects the power delivery assembly to the UV lamp.

Clause 9. The powering device of Clause 8, wherein the coupler comprises a twisted pair of insulated wires.

Clause 10. The powering device of Clause 8, wherein the coupler comprises a coaxial cable including an insulation layer and a metallic shielding layer that surrounds the insulation layer.

Clause 11. The powering device of any of Clauses 1-10, further comprising a transformer disposed between the power delivery assembly and the UV lamp.

Clause 12. The powering device of any of Clauses 1-11, further comprising a power boost switch selectively actuatable to command a temporary power increase from the power delivery assembly to the UV lamp.

Clause 13. The powering device of any of Clauses 1-12, wherein the power delivery assembly comprises an external power interface, a charger, a battery pack, and at least one capacitor, wherein the charger is configured to receive electric current from the external power interface and supply the electric current to at least one of the battery pack or the at least one capacitor.

Clause 14. A method of providing power to an ultraviolet (UV) lamp of a sanitizing system, the method comprising:

providing, by a power delivery assembly of a powering device, power to the UV lamp; and controlling, from a power controller coupled to the power delivery assembly, one or more aspects of the power provided from the power delivery assembly to the UV lamp.

Clause 15. The method of Clause 14, further comprising:

coupling one or more potentiometers to the power controller; and adjusting or otherwise controlling, by the one or more potentiometers, frequency, pulse width modulation, and current with respect to the power provided to the UV lamp.

Clause 16. The method of Clause 14 or 15, further comprising connecting, by a coupler, the power delivery assembly to the UV lamp.

Clause 17. The method of any of Clauses 14-16, further comprising disposing a transformer between the power delivery assembly and the UV lamp.

Clause 18. A powering device configured to provide power to an ultraviolet (UV) lamp of a sanitizing system, the powering device comprising:

a power delivery assembly configured to provide power to the UV lamp, the power delivery assembly including a battery pack and at least one capacitor;

a power controller coupled to the power delivery assembly, wherein the power controller is configured to control one or more aspects of the power provided from the power delivery assembly to the UV lamp;

one or more potentiometers coupled to the power controller, wherein the one or more potentiometers are configured to adjust or otherwise control frequency, pulse width modulation, and current with respect to the power provided to the UV lamp;

a transformer disposed between the power delivery assembly and the UV lamp, the at least one capacitor configured to receive electric current from the battery pack and supply the electric current to the transformer; and a coupler that connects the transformer to the UV lamp, wherein the coupler includes at least one insulated wire that is surrounded by a metallic shielding layer.

Clause 19. The powering device of Clause 18, wherein the at least one insulated wire of the coupler comprises a twisted pair of two insulated wires.

Clause 20. The powering device of Clause 18 or 19, wherein the power delivery assembly further comprises an external power interface and a charger, the external power interface configured to connect to an external power source, the charger configured to receive electric current from the external power source, via the external power interface, and supply the electric current to at least one of the battery pack or the at least one capacitor.

As described herein, embodiments of the present disclosure provide systems and methods for providing power to a UV lamp, such as a 222 nm excimer lamp of a wand assembly of a portable sanitizing system.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A powering device configured to provide power to an ultraviolet (UV) lamp of a sanitizing system, the powering device comprising:
   a power delivery assembly configured to provide power to the UV lamp;
   a power controller coupled to the power delivery assembly, wherein the power controller is configured to control one or more aspects of the power provided from the power delivery assembly to the UV lamp; and
   a power boost switch selectively actuatable to command a temporary power increase from the power delivery assembly to the UV lamp.

2. The powering device of claim 1, wherein the UV lamp is within a sanitizing head of a wand assembly.

3. The powering device of claim 2, wherein the powering device is within a backpack assembly coupled to the wand assembly.

4. The powering device of claim 1, wherein the UV lamp is an excimer lamp configured to emit UV light having a wavelength of 222 nm.

5. The powering device of claim 1, further comprising one or more potentiometers coupled to the power controller and configured to adjust or otherwise control frequency, pulse width modulation, and current with respect to the power provided to the UV lamp.

6. The powering device of claim 1, wherein the power delivery assembly includes a battery pack and at least one capacitor, the at least one capacitor configured to receive electric current from the battery pack and supply the electric current to a transformer.

7. The powering device of claim 1, further comprising:
   a power switch; and
   a lamp power switch.

8. The powering device of claim 1, further comprising a coupler that connects the power delivery assembly to the UV lamp.

9. The powering device of claim 8, wherein the coupler comprises a twisted pair of insulated wires.

10. The powering device of claim 8, wherein the coupler comprises a coaxial cable including an insulation layer and a metallic shielding layer that surrounds the insulation layer.

11. The powering device of claim 1, further comprising a transformer disposed between the power delivery assembly and the UV lamp.

12. The powering device of claim 1, wherein the power delivery assembly comprises an external power interface, a charger, a battery pack, and at least one capacitor, wherein the charger is configured to receive electric current from the external power interface and supply the electric current to at least one of the battery pack or the at least one capacitor.

13. A powering device configured to provide power to an ultraviolet (UV) lamp of a sanitizing system, the powering device comprising:
   a power delivery assembly configured to provide power to the UV lamp, the power delivery assembly including a battery pack and at least one capacitor;
   a power controller coupled to the power delivery assembly, wherein the power controller is configured to control one or more aspects of the power provided from the power delivery assembly to the UV lamp;
   one or more potentiometers coupled to the power controller, wherein the one or more potentiometers are configured to adjust or otherwise control frequency, pulse width modulation, and current with respect to the power provided to the UV lamp;
   a transformer disposed between the power delivery assembly and the UV lamp, the at least one capacitor configured to receive electric current from the battery pack and supply the electric current to the transformer; and
   a coupler that connects the transformer to the UV lamp, wherein the coupler includes at least one insulated wire that is surrounded by a metallic shielding layer.

14. The powering device of claim 13, wherein the at least one insulated wire of the coupler comprises a twisted pair of two insulated wires.

15. The powering device of claim 13, wherein the power delivery assembly further comprises an external power interface and a charger, the external power interface configured to connect to an external power source, the charger configured to receive electric current from the external power source, via the external power interface, and supply the electric current to at least one of the battery pack or the at least one capacitor.

16. A powering device configured to provide power to an ultraviolet (UV) lamp of a sanitizing system, the powering device comprising:
   a power delivery assembly configured to provide power to the UV lamp;
   a power controller coupled to the power delivery assembly, wherein the power controller is configured to control one or more aspects of the power provided from the power delivery assembly to the UV lamp; and
   a coupler that connects the power delivery assembly to the UV lamp, wherein the coupler comprises a coaxial cable including an insulation layer and a metallic shielding layer that surrounds the insulation layer.

17. The powering device of claim 16, wherein the UV lamp is within a sanitizing head of a wand assembly.

18. The powering device of claim 16, further comprising one or more potentiometers coupled to the power controller and configured to adjust or otherwise control frequency, pulse width modulation, and current with respect to the power provided to the UV lamp.

19. The powering device of claim 16, wherein the power delivery assembly includes a battery pack and at least one capacitor, the at least one capacitor configured to receive electric current from the battery pack and supply the electric current to a transformer.

20. The powering device of claim 16, wherein the power delivery assembly comprises an external power interface, a charger, a battery pack, and at least one capacitor, wherein the charger is configured to receive electric current from the external power interface and supply the electric current to at least one of the battery pack or the at least one capacitor.

* * * * *